(12) United States Patent
Oda et al.

(10) Patent No.: US 8,345,941 B2
(45) Date of Patent: Jan. 1, 2013

(54) BIOLOGICAL IMAGING DEVICE

(75) Inventors: Ichiro Oda, Kyoto (JP); Atsushi Yajima, Kyoto (JP); Kentaro Hizumi, Kyoto (JP); Akimasa Mega, Kyoto (JP); Tadafumi Kamikake, Kyoto (JP); Yutaka Kuratani, Kyoto (JP); Takeshi Fujita, Kyoto (JP); Yoshio Tsunazawa, Kyoto (JP)

(73) Assignee: Shimadzu Corporation, Tokyo (JP)

( * ) Notice: Subject to any disclaimer, the term of this patent is extended or adjusted under 35 U.S.C. 154(b) by 185 days.

(21) Appl. No.: 12/992,560

(22) PCT Filed: May 15, 2008

(86) PCT No.: PCT/JP2008/058921
§ 371 (c)(1),
(2), (4) Date: Dec. 16, 2010

(87) PCT Pub. No.: WO2009/139058
PCT Pub. Date: Nov. 19, 2009

(65) Prior Publication Data
US 2011/0096967 A1    Apr. 28, 2011

(51) Int. Cl.
*G06K 9/00* (2006.01)
(52) U.S. Cl. .......................... 382/128; 377/10; 348/135
(58) Field of Classification Search .................. 382/100, 382/128, 129, 130, 131, 132, 133, 134, 103; 377/10; 348/135, 169–172
See application file for complete search history.

(56) References Cited

U.S. PATENT DOCUMENTS

| | | | |
|---|---|---|---|
| 6,819,411 B1 * | 11/2004 | Sharpe et al. | 356/72 |
| 7,221,453 B2 | 5/2007 | Sharpe et al. | 356/338 |
| 7,586,604 B2 * | 9/2009 | Sharpe et al. | 356/338 |
| 7,603,167 B2 * | 10/2009 | Stearns et al. | 600/473 |
| 2003/0076500 A1 | 4/2003 | Nanami et al. | 356/436 |
| 2005/0110996 A1 | 5/2005 | Sharpe et al. | 356/338 |
| 2005/0201614 A1 * | 9/2005 | Rice et al. | 382/154 |
| 2007/0285662 A1 | 12/2007 | Sharpe et al. | 356/337 |
| 2008/0317313 A1 * | 12/2008 | Goddard et al. | 382/131 |
| 2009/0086314 A1 * | 4/2009 | Namba et al. | 359/383 |
| 2009/0252682 A1 * | 10/2009 | Hillman | 424/9.1 |

FOREIGN PATENT DOCUMENTS

| | | |
|---|---|---|
| JP | 09-184808 | 7/1997 |
| JP | 11-326008 | 11/1999 |
| JP | 2001-330915 | 11/2001 |
| JP | 2002-228578 | 8/2002 |
| JP | 2007-183655 | 7/2007 |

* cited by examiner

*Primary Examiner* — Anand Bhatnagar
(74) *Attorney, Agent, or Firm* — DLA Piper LLP (US)

(57) ABSTRACT

Optical waveguide paths to observe a sample on a sample holder from a plurality of directions while guiding an image of light in each direction which is emitted out of the sample toward a direction of a two dimensional detector via a main imaging lens include an optical waveguide path which never receives the light directly from the sample. The optical waveguide path which never receives the light directly from the sample forms an image of the sample within a substantial focus range of the main imaging lens, and includes optical elements arranged such that a light beam after formation of the image proceeds toward a direction of the main imaging lens. Optical elements on at least one optical waveguide path are those for forming real images. Therefore, the main imaging lens images the sample and those real images in block on the two dimensional detector.

23 Claims, 29 Drawing Sheets

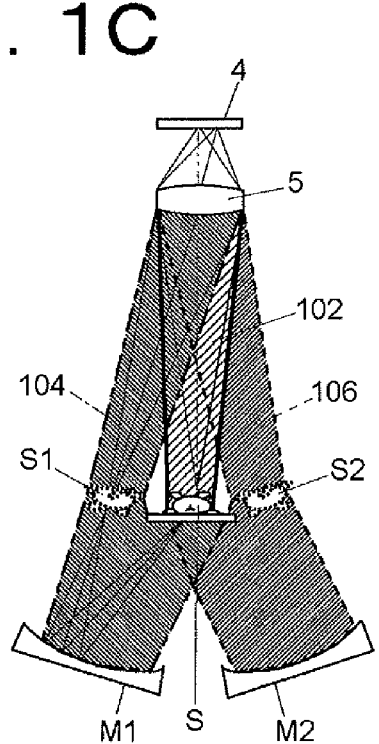

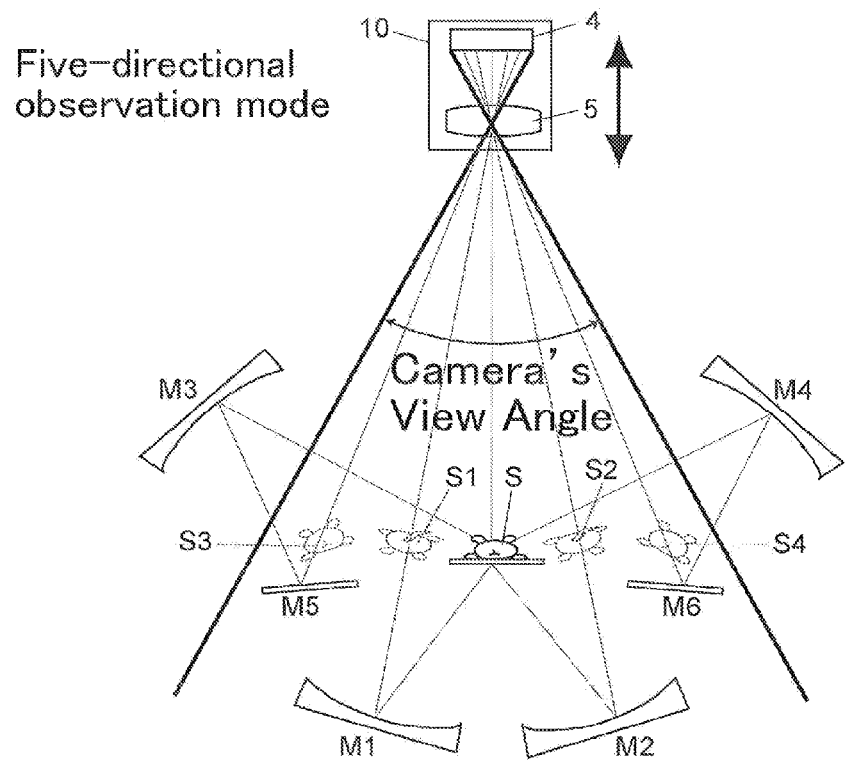

One-directional observation mode

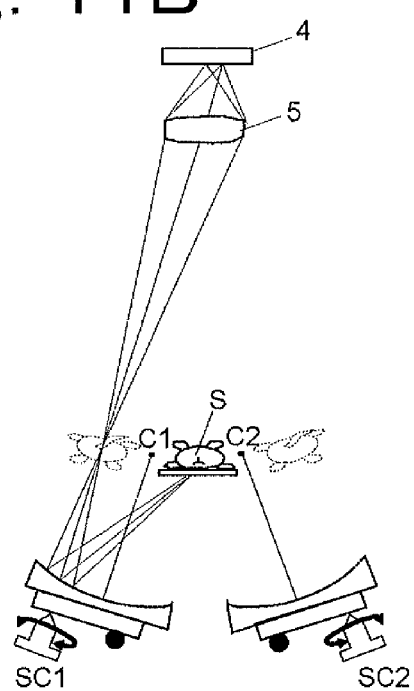

$\beta = \angle QGP$
$R = QG = GP$

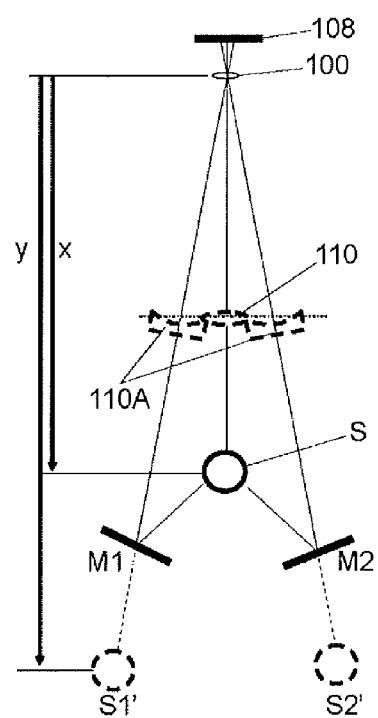

BIOLOGICAL IMAGING DEVICE

CROSS-REFERENCE TO THE RELATED APPLICATIONS

This application is a national stage of international application No. PCT/JP2008/058921, filed on May 15, 2008, the entire contents of which are incorporated herein by reference.

BACKGROUND OF THE INVENTION

1. Field of the Invention

The present invention relates to an optical bioimaging technology for biological samples such as small animals.

2. Description of the Related Art

In medical and biological fields, imaging of the distribution of molecular species in a living body is an important research technique. Heretofore, cellular-level imaging of molecular species has been widely performed using a microscope and a molecular probe labeled with fluorochrome or a chemiluminescent molecular probe. Hereafter, there is a demand for a device capable of observing the distribution of molecular species of interest in a living body not at the cellular level but at the level of organ or the entire animal body larger than cells. Such a device makes it possible to acquire images of a living body, such as a mouse, whose cancer cells are labeled with fluorescent probes every day or every week to monitor the growth of cancer cells of interest with the lapse of time. In a case where the growth of cancer cells in the body of an animal is observed by a conventional cellular-level observation device, it is necessary to kill the animal to stain a site to be observed or to attach a fluorescent substance to cancer cells. In this case, however, it is impossible to monitor the growth of cancer cells in the same animal body over a long period of time. For this reason, there is a demand for development of a device capable of observing molecular species in the body of a small live animal to obtain internal information of the small animal.

Near-infrared light relatively easily penetrates a living body. Therefore, light ranging from about 600 nm to 900 nm is used in devices for observing small animals. However, according to a conventional observation technique, a specimen is usually observed only from above, and cannot be simultaneously observed from various directions. Therefore, there is a case where, for example, when a mouse is observed from a specific direction, cancer is not detected, but when the mouse is observed from a direction opposite to the specific direction, cancer is detected. When a mouse is observed using an unidirectional observation device, an operator has no choice but to observe the mouse by a method approximate to multi-directional observation by picking up multi-directional images of the mouse rotated about its body axis by small increments. However, in this case, reproducible data cannot be obtained, and the mouse cannot be simultaneously observed from various directions. Particularly, in the case of observation of luminescence emitted from a living body, the intensity of luminescence is very weak, and therefore, it is usually necessary to perform integrated exposure on a two-dimensional detector for several tens of seconds to a few minutes. On the other hand, the intensity of luminescence changes with time, and therefore, when image pickup is performed every time the observation direction is changed, image pickup conditions are different among image pickup directions, and thus, resulting images are useless. For this reason, it is preferred that two or more images of a living body picked up from two or more directions can be simultaneously and parallely integrated on a detector for a long period of time. In the case of fluorescence measurement, light intensity is higher than that in luminescence measurement, and therefore, fluorescence images can be acquired in a relatively short period of time. Still, it is absolutely necessary to simultaneously pick up information from various directions to speedily obtain accurate data.

As a method for acquiring multi-directional images, one for sequentially acquiring images observed from various angles using a rotating reflection mirror in a time-sharing manner is known (see Patent Document 1). According to this method, a specimen can be observed from various directions by rotating the mirror and by changing the position of the specimen itself by parallel displacement, and therefore, it is not necessary to rotate the specimen or a two-dimensional detector.

However, the method disclosed in Patent Document 1 uses a rotating reflection mirror and therefore has the following drawbacks: a specimen is measured from various directions in a time-sharing manner, that is, multi-directional simultaneous measurement cannot be performed, and therefore, it takes a long time to complete measurement; images observed from different directions are picked up at different times, and therefore, measurement conditions vary according to time in the case of, for example, luminescence measurement because the intensity of luminescence changes with time; and a device using a rotating reflection mirror has a complicated structure.

On the other hand, as a method for simultaneously acquiring images observed from various directions, a method using a back-side mirror unit is known (see Patent Document 2). Patent Document 2 discloses a method for simultaneously acquiring multi-directional images of a sample constituting a 3D-image by picking up not only a front-side image but also a back-side image and a lateral-side image with the use of an imaging lens and two or more mirrors provided on the back side of the sample. However, in this case, the distance between the imaging lens and a virtual image formed by the mirror is larger than that between the imaging lens and the sample. Therefore, the imaging lens cannot simultaneously focus both direct light from the sample and light reflected by the back-side mirror toward the lens. In 3D-image acquisition, a focal point range, that is, the so-called depth of focus can be usually widened by stopping down a lens. Therefore, such multi-directional simultaneous measurement as disclosed in Patent Document 2 is achieved based on the premise that multi-directional images can be acquired even when virtual image is located at different distances of sample. That is, it can be considered that such a camera for acquiring 3D-image data is constructed on the premise that its lens is stopped down to increase the depth of focus.

Patent Document 1: U.S. Patent Application No. 20050201614

Patent Document 2: Japanese Patent Application Laid-open No. 2001-330915

SUMMARY OF THE INVENTION

However, the biological imaging device according to the present invention intended for biological fluorescence imaging or biological luminescence imaging needs to measure weak light and therefore requires a large-aperture lens. More specifically, the biological imaging device according to the present invention typically requires not a small-aperture lens such as a video camera lens having a focal length f of 15 mm and an aperture of F/8 (in this case, the actual aperture of the lens is only about 2 mm (i.e., 15/8)) but a lens having a focal length f of about 50 mm and an aperture of F/1 to F/2 (i.e., the actual aperture of the lens is about 50 mm to 25 mm). That is, the actual aperture of a lens used for luminescence measurement or fluorescence measurement is about an order of magnitude greater than that of a lens for 3D-image acquisition determined based on preconditions for 3D-image measurement. Since the depth of focus is inversely proportional to the actual aperture of a lens, a camera for 3D-image acquisition has a large depth of focus and therefore no problem is caused even when the distance between a lens and an object (sample or its image) slightly varies. However, the biological imaging device according to the present invention intended for biological fluorescence imaging or biological luminescence imaging needs to be designed based on the premise that it is a multi-directional image acquisition device using a bright large-aperture lens having a small depth of focus.

As a technique for solving the problem described above with reference to Patent Document 2, that is, the problem that a main imaging lens cannot simultaneously focus on both a sample and an image of the sample formed by a reflection mirror, which is placed on the back side of the sample, at a distance from the sample, a technique using an auxiliary lens may be employed. In this case, an auxiliary lens is provided midway in an optical path to shift either a sample itself or its image formed by a reflection mirror in the back-and-forth direction of a main imaging lens. This technique will be described with reference to FIG. 16A. FIG. 16A shows a measurement system for simultaneously acquiring images of a sample S observed from three directions, including the front direction of the sample S, with the use of plane mirrors M1 and M2 arranged to observe the sample S from obliquely below.

As shown in FIG. 16A, a virtual image S1' of the sample S is formed by the plane mirror M1 and a virtual image S2' of the sample S is formed by the plane mirror M2. At this time the distance between a main imaging lens 100 and the image S1' or S2' (represented as "y" in FIG. 16A) is much larger than the distance between the main imaging lens 100 and the sample S (represented as "x" in FIG. 16A).

As a means for eliminating the difference between the distance x and the distance y, a convex lens 110 as an auxiliary lens is provided in an optical path for guiding a front-side image of the sample S to the main imaging lens 100, or concave lenses 110A as auxiliary lenses are provided in optical paths for guiding images of the sample S observed from obliquely below to the main imaging lens 100. The convex lens 110 has the function of increasing the distance x so that the distance x becomes equal to the distance y between the main imaging lens 100 and the back-side image of the sample S. On the contrary, the concave lens 110A has the function of decreasing the distance y so that the distance y becomes equal to the distance x between the main imaging lens 100 and the front-side image of the sample S.

The technique using an auxiliary lens is effective to some extent. In a case where the aperture of the main imaging lens 100 is in the range of about 2 mm to 20 mm, this technique is sufficiently useful for practical purposes because drawbacks associated with using an auxiliary lens are relatively minor. However, it has been found that this technique cannot be used when a lens having an aperture larger than about 20 mm (e.g., a large-aperture lens having an aperture of 40 mm to 50 mm (focal length: about 50 mm, F value: about 1 to 1.2)) is used. The reason for this will be described below with reference to FIGS. 16B and 16C.

FIGS. 16B and 16C show the same three-directional measurement system as shown in FIG. 16A, wherein the convex lens 110 as an auxiliary lens is provided midway in the optical path for guiding the front-side image of the sample S. Hereinbelow, problems that will occur when the main imaging lens 100 has a large aperture will be described with reference to a comparison between a case where the main imaging lens 100 has a small aperture (FIG. 16B) and a case where the main imaging lens 100 has a large aperture (FIG. 16C).

As shown in FIGS. 16B and 16C, in either case, virtual images of the sample S are formed by the reflection mirrors M1 and M2 below the sample S at positions S1' and S2'. When the auxiliary lens 110 is provided in the optical path for guiding the front-side image of the sample S to shift the position of the sample S to the position of the virtual image formed by the reflection mirror, the two virtual images and an image S0' formed by the auxiliary lens 110 are located at the same distance from the main imaging lens 100. At this time, the image S0' is (b/a) times larger than the sample S due to magnification by the auxiliary lens 110. Here, "a" represents the distance between the auxiliary lens 110 and the sample S and "b" represents the distance between the auxiliary lens 110 and the image S0'.

In this case, a first problem is that the front-side image is extremely large, but on the contrary, the back-side images become smaller.

The second problem is that optical waveguide paths 104 and 106 for guiding the back-side image of the sample S to the main imaging lens 100 and an optical waveguide path 102 for guiding the front-side image of the sample S to the main imaging lens 100 overlap with each other at the position of the auxiliary lens 110. In FIGS. 16B and 16C, these optical waveguide path are marked with diagonal lines. As shown in FIG. 16B, when the main imaging lens 100 has a small aperture, the optical waveguide paths 102, 104, and 106 do not overlap with each other at the auxiliary lens 110. However, as shown in FIG. 16C, when the main imaging lens 100 has a large aperture, the optical waveguide paths 102, 104, and 106 overlap with each other at the auxiliary lens 110.

In the above description, the area represented by the reference numeral 102, 104, or 106 has been expressed as an "optical waveguide path". In the following description, the whole path region for guiding an image observed from each direction is defined as an "optical waveguide path". Hereinbelow, the formation of images observed from different directions and the above-described second problem will be described using the term "optical waveguide path".

Image information is carried by a plurality of light beams emitted from each point on the sample. These light beams travel in the optical waveguide paths, enter the main imaging lens 100, and then reach a two-dimensional detector 108. If necessary, each of the optical waveguide paths may include an optical element for reflecting or refracting light to guide the light to the main imaging lens 100. That is, the number of optical waveguide paths is equal to that of observation directions, and a plurality of light beams are present in the optical waveguide paths. Each of the optical waveguide paths includes a space enclosed with outermost light beams present in the optical waveguide path and, if necessary, the optical element. The optical waveguide path 102 for guiding the front-side image of the sample S includes no optical element between the sample and the main imaging lens 100, and therefore includes only an open space. Such an optical waveguide path including no optical element is also defined as an "optical waveguide path" for the purpose of uniformity in description. That is, not all the optical waveguide path include the optical element.

As can be seen from a comparison between FIG. 16B and FIG. 16C, when the main imaging lens has a small aperture (FIG. 16B), the degree of overlapping between the optical waveguide paths is small, but when the main imaging lens has a large aperture (FIG. 16C), the degree of overlapping between the optical waveguide paths is large. However, the problem is that whether the optical waveguide paths overlap with each other at a position where the auxiliary lens should be provided, that is, whether there is enough space to provide the auxiliary lens in a region where the optical waveguide paths do not overlap with each other. In order to more accurately describe the positional relationship between the auxiliary lens and the optical waveguide paths, attention is given to light beams passing through both ends of the optical waveguide path.

In the case shown in FIG. 16B, there is a space between a straight line C'B (i.e., a straight line connecting the right edge C' of the image S1' formed by the reflection mirror M1' and the right edge B of the main imaging lens 100) and a straight line D'A (i.e., a straight line connecting the left edge D' of the enlarged image of the sample formed by the auxiliary lens 110 and the left edge A of the main imaging lens 100) at the position of the auxiliary lens 110, but in the case shown in FIG. 16C, there is no space between the straight line C'B and the straight line D'A. When the optical waveguide paths overlap with each other at the position of the auxiliary lens 110, sample image S and virtual image S' overlap each other on a two-dimensional detector. Therefore, the auxiliary lens 110 needs to be arranged at a position where the optical waveguide paths do not overlap with each other. When the auxiliary lens 110 is arranged at a position closer to the sample S, a slightly larger space to arrange the auxiliary lens 110 can be secured. However, in this case, the distance "a" between the auxiliary lens 110 and the sample S is smaller, and therefore, the front-side image of the sample S is further enlarged due to a higher magnification (b/a), which makes the first problem more serious. As can be seen from the example shown in FIGS. 16B and 16C, a multi-faceted mirror system using the main imaging lens 100 having an aperture larger than a certain level cannot be constructed, as long as the auxiliary lens 110 is provided between the sample S and the main imaging lens 100. It is to be noted that the above description has been made with reference to a case where the convex lens 110 is provided as an auxiliary lens in the optical waveguide path 102 for guiding the front-side image of the sample S, but also in a case where the concave lenses 110A, shown in FIG. 16A are provided in the optical waveguide paths 104 and 106 for guiding the back-side image of the sample S observed from obliquely below, overlapping between the optical waveguide path occurs at the position of the concave lens, and therefore, a large-aperture lens cannot be used as the main imaging lens 100.

As described above, when only plane mirrors are provided to acquire back-side images of a sample, the images are formed far from the sample, which makes it impossible for an imaging lens to focus on all the images observed from different directions. This problem can be alleviated by using an auxiliary lens, but in this case, the aperture of the imaging lens is limited, which makes it impossible to construct a bright image acquisition system.

It is therefore an object of the present invention to provide a biological imaging device for multi-directional simultaneous observation having a bright optical system for guiding light beams emitted in various directions to different positions on a two-dimensional detector.

In order to achieve the above object, the present invention is directed to a biological imaging device, comprising: a sample holder on which a biological sample is to be placed; a two-dimensional detector that detects an image of light emitted from a sample placed on the sample holder; optical waveguide paths provided in different directions to observe a sample placed on the sample holder from two or more directions and to guide images of light emitted from the sample in different directions to the two-dimensional detector; and a main imaging lens arranged between the two-dimensional detector and the optical waveguide paths to form images guided by the optical waveguide paths at different positions on the two-dimensional detector according to an observation direction.

In such a biological imaging device, at least one of the optical waveguide paths is an optical waveguide path not receiving direct light from a sample, and the optical waveguide path not receiving direct light from the sample includes an optical element provided to form an image of the sample within a substantial focus range of the main imaging lens and to allow light beams from the image to travel toward the main imaging lens, and the optical element is an optical element that forms a real image as the image.

Therefore, images of the sample observed from two or more directions are guided by the optical waveguide paths, and are then simultaneously formed by the main imaging lens on the two-dimensional detector.

As has been described above, the use of only plane mirrors is advantageous in that aberration does not occur at all, but when the back side of a sample is observed using plane mirrors, only virtual images are formed below the sample, and, in addition, the virtual images are far from the sample, and therefore, it is difficult for a main imaging lens to properly focus on all the images observed from different directions. Such a problem can be alleviated by using an auxiliary lens, but in this case, the aperture of the imaging lens is limited. For this reason, the present invention takes the following measures.

First Principle of the Present Invention—Use of Imaging Optical System

According to the present invention, an optical element that forms a real image, such as a concave mirror, is provided instead of a plane mirror in an optical waveguide path provided in a direction where, when a plane mirror is used to observe a sample, an image is formed far from the sample. This makes it possible to form not a virtual image but a real image of a sample so that the real image and the sample are at substantially the same distance from a main imaging lens.

The first principle of the present invention will be described with reference to FIGS. 1A to 1D. Here, the optical element that forms a real image will be described with reference to a concave mirror, but is not limited thereto. The first principle of the present invention can be achieved also by using an optical element obtained by, for example, combining a plane mirror and a convex lens. FIG. 1A is a perspective view of an optical system for explaining the first principle, FIG. 1B is a front sectional view of the optical system shown in FIG. 1A, and FIG. 1C is a front sectional view of the optical system shown in FIG. 1A, which shows optical waveguide paths. The optical system shown in FIGS. 1A to 1C uses a CCD 4 as an example of the two-dimensional detector. Further, the optical system shown in FIGS. 1A to 1C uses large concave mirrors M1 and M2 instead of the plane mirrors M1 and M2 shown in FIG. 16A to guide back-side images of a sample S to the CCD. In this case, inverted real images S1 and S2 of the sample S are formed on opposite sides of the sample S, and three images including a directly-observed image of the sample S and the two real images S1 and S2 are picked up from above by a main imaging lens 5 and the CCD 4. The sample S and the two real images S1 and S2 are at substantially the same distance from the main imaging lens 5. Therefore, unlike the case shown in FIG. 16A, it is not necessary to insert focusing auxiliary lenses in optical waveguide paths provided in different directions, and therefore, overlapping between the optical waveguide paths causes no problem, which makes it possible to use a large-aperture lens as the main imaging lens 5. As can be seen from a comparison between FIG. 1C and FIG. 16B, in the optical system shown in FIG. 16B, the images S1' and S2' are farther from the main imaging lens than the sample S0', and therefore, the auxiliary lens 110 needs to be used to allow the sample S and the images S1' and S2' to be forcibly arranged at the same distance from the main imaging lens, but the optical waveguide paths overlap with each other at the position of the auxiliary lens 110. On the other hand, the optical system shown in FIG. 1C is originally configured to allow the sample S and the images S1' and S2' to be arranged at substantially the same distance from the main imaging lens 5, which eliminates the necessity to use an auxiliary lens. Therefore, overlapping between the optical waveguide paths does not cause any problem. That is, also in the case shown in FIG. 1C, three optical waveguide paths 102, 104, and 106 marked with diagonal lines overlap with each other in front of the main imaging lens, but it is not necessary to provide any optical elements at a position where the optical waveguide paths overlap with each other, which is a main different from the optical system shown in FIG. 16A.

The two main points of imaging using the optical system shown in FIGS. 1A and 1B are as follows:

1) A position C1 of the center of curvature of the concave mirror M1 and a position C2 of the center of curvature of the concave mirror M2 are important. That is, it is important that a point on the sample S and a corresponding point on its image S1' are three-dimensionally symmetrical to each other with respect to the position C1 and a point on the sample S and a corresponding point on its image S2' are three-dimensionally symmetrical to each other with respect to the position C2. For example, assuming that the main imaging lens 5 focuses on a point Q, a chief ray (light that passes through the center of the imaging lens 5) traveling in the reverse direction (i.e., from the imaging lens 5 to the sample S) impinges on the concave mirror M1 at a point G located on an imaginary line extending from the point Q, and is reflected by the concave mirror M1 toward a point P on the sample S. At this time, the incident angle equals the reflected angle, and therefore, the center of curvature C1 of the mirror M1 is the midpoint between the point P and the point Q. That is, the reflected light from the point G travels toward the point P symmetrical to the point Q with respect to the center of symmetry C1. In a case where the sample S to be measured is, for example, a mouse, when the point P is located on the lower surface of the head of the mouse as shown in FIG. 1A, the point Q is located on the lower side of the head of the inverted image S1 in which the abdomen of the mouse faces the lens 5. When the mouse is observed through the main imaging lens 5, as shown in FIG. 1D, a front-side image showing the dorsal side of the mouse and two back-side images showing the ventral side of the mouse can be obtained. The back-side images are formed on opposite sides of the front-side image, and as can be seen from FIG. 1D, the points P and Q are symmetrical to each other with respect to the point C1. Similarly, another point on the sample S, for example, a point H is mapped onto a point I on the image S2 symmetrical to the point H with respect to the point C2.

It is to be noted that when the positions of the points C1 and C2 are moved closer to the sample S, the images S1 and S2 as a whole are moved closer to the sample S, and when the positions of the points C1 and C2 are moved away from the sample S, the images S1 and S2 are also moved away from the sample S. That is, the positions of the images S1 and S2 can be adjusted by changing the positions of the points C1 and C2, and therefore, the images observed from various directions can be arranged in a balanced manner within the field of view of a camera.

2) The second point relates to the imaging characteristics of the optical element that forms a real image. When a real image of a sample is formed using a large optical element such as the concave mirror M1 or M2, a very large aberration generally occurs. For example, when a "sheet of paper" is placed in the position of the image S1 in FIG. 1A, the image S1 formed on the sheet of paper is blurred because the entire surface of the concave mirror M1 is used, and therefore, a large aberration occurs. However, in fact, the image S1 is viewed through the main imaging lens 5, and therefore, when the main imaging lens 5 focuses on, for example, the point Q, only light beams from a part having an area $\delta S$, whose center is the point G at which an imaginary line extending from the point Q intersects the mirror M1, enter the main imaging lens 5. That is, only a part of the large concave mirror M1, i.e., a small concave mirror represented by $\delta S$ is used for imaging. Therefore, a solid angle $\omega$ for imaging is a relatively small value (corresponding to an F value of about 6 or greater), and thus aberration falls within a practically acceptable range even when such a large concave mirror is used. When the point Q to be measured is moved, the part $\delta S$ of the concave mirror M1 corresponding to the point Q is also moved together with the point Q throughout the concave mirror M1, but the concave mirror M1 used for imaging is limited to a range having the above-mentioned area $\delta S$ irrespective of the position of the point Q.

Conveniently, aberration can be reduced by imaging at a magnification of 1:1 (1:1 imaging) using a spherical concave mirror. Especially, when the point P and the point Q are close to each other (i.e., when an angle formed by Q, G, and P is small), a clearer image can be formed. In an extreme case where an angle formed by Q, G, and P is close to zero, a state where light emitted from the center of curvature of a spherical concave mirror returns to the same point is substantially achieved. In this case, aberration does not occur. As can be seen from this example, 1:1 imaging using a spherical concave mirror is advantageous from the viewpoint of aberration.

As shown in FIG. 1A, when the images S1 and S2 have the same size as the sample S (1:1), three images (including the sample S) having the same size are again formed by the imaging lens 5 on the CCD 4, and therefore, three images well-balanced in size can be obtained. In addition to that, as described above, 1:1 imaging is advantageous from the viewpoint of aberration. These good fortunes make the use of a spherical concave mirror as an optical element advantageous. That is, a point to be emphasized is that a sufficient advantage can be obtained by a cheap spherical concave mirror with no need to use a non-spherical (e.g., ellipsoid) concave mirror. Further, in the following paragraph "function", aberration by 1:1 imaging and changes in aberration when an angle $\beta$ (i.e., an angle formed by Q, G, and P) is slightly increased are determined by a little more complicated calculation to provide guidelines for the arrangement of a concave mirror in an optical system to take advantage of characteristics of the concave mirror.

As described above, the first principle of the present invention is the principle of use of an imaging optical element for directing the back-side image of a sample toward the CCD. It is to be noted that the use of large concave mirrors as the concave mirrors M1 and M2 shown in FIG. 1A is meaningful. The reason for this will be described below. When one point (e.g., the point Q) on the image S1 of the sample S is viewed through the main imaging lens 5, the point G is present on the concave mirror located behind the image S1. That is, the concave mirror M1 needs to be large to such an extent that the point G can be present on the concave mirror M1. When it is necessary to observe the entire image S1 of the sample in the case shown in FIG. 1A, the size of the concave mirror M1 as a whole is about 1.5 times that of the image S1. This is because the concave mirror M1 needs to be large to such an extent that, when viewed through the lens 5, it can be seen behind the image S1 of the sample. In a case where not the entire of the image S1 of the sample but part of the image S1 (e.g., only the head) is observed, smaller concave mirrors may be used as the concave mirrors M1 and M2 (which will be described later). That is, the size of a concave mirror used can be selected according to the purpose of measurement.

A second principle of the present invention relates to a method for placing an image, which is formed by an imaging optical element arranged in an observation direction, at a desired position in open space within the field of view of a camera by additionally using a "bending plane mirror" which will be described later.

In the case shown in FIG. 1A, based on the first principle, light beams passing through an image (e.g., the image S1) formed by the concave mirror M1, which is one example of the imaging optical element, travel upward toward the main imaging lens 5, and therefore, the concave mirror M1 needs to be arranged "behind" the image S1 when viewed through the main imaging lens 5. In this case, the concave mirror M1 faces the back side of the sample S, and therefore can only be used for observation from the back side of the sample S. Such limitation is removed by a technique based on the second principle, that is, by a "technique for allowing a sample to be observed from a lateral direction or an obliquely upward direction in spite of using a concave mirror by directing the image S1 formed by the concave mirror toward the main imaging lens while allowing the image S1 to be formed at a desired position within the field of view of the CCD". This technique is achieved by using a concave mirror and an additional "bending plane mirror" in combination.

The second principle will be described with reference to FIG. 2. In FIG. 2, the sample S is represented as a cylinder, and an imaginary concave mirror M1$a$ corresponds to the concave mirror M1 shown in FIG. 1A for observing the back side of the sample S from the direction of an angle $\alpha 0$. The issue that needs to be addressed by the second principle is to change the observation direction of an angle $\alpha 0$ to the observation direction of an angle $\alpha$. Therefore, the concave mirror M1 is arranged in the direction of a desired observation angle $\alpha$. In the case shown in FIG. 2, $\alpha$ is set to just 90°, and therefore, observation of the sample S from the lateral direction can be achieved. In FIG. 2, the concave mirror M1 is arranged so as to be symmetrical to the imaginary concave mirror M1$a$ with respect to the plane of a "bending plane mirror" M3, and therefore, when an angle between the plane mirror M3 and the vertical line is defined as $\theta$, $\theta$, $\alpha$, and $\alpha 0$ should satisfy the following relationship from the viewpoint of symmetry:

$$\alpha - \theta = \theta - \alpha_0, \text{ that is, } \alpha = 2\theta - \alpha_0 \quad (1)$$

or $$\theta = (\alpha + \alpha_0)/2 \quad (1')$$

That is, a desired observation angle $\alpha$ can be achieved by determining the angle $\theta$ of the "bending plane mirror" M3 using the formula (1'). On the other hand, when the angle $\theta$ is already decided, the observation angle $\alpha$ can be determined using the formula (1).

It can be said that this is a technique in which the concave mirror M1 is first arranged in a direction of a desired observation angle $\alpha$ and then one bending mirror is arranged so that the concave mirror M1 can be seen behind the image S1 when viewed through the camera 4.

It is to be noted that light emitted from the attention point P on the sample S shown in FIG. 2 is focused in the following manner. An image of the attention point P is formed at a point Q' by the concave mirror M1, but the position of the image is changed to the position of a point Q by the bending mirror M3. Then, light beams travel toward the main imaging lens 5 and are again focused by the main imaging lens 5 on the two-dimensional detector.

Variation of Second Principle (Combined Use of Two Bending Mirrors)

A variation of the second principle is the same as the second principle in that a real image of the sample S is formed at a position of S1. However, the variation of the second principle uses two bending mirrors in combination to remove the above-described limitation that "a concave mirror is arranged in a direction of a desired observation angle $\alpha$". The variation of the second principle will be described with reference to FIG. 3A showing a case where the sample S is observed from directly below (i.e., from the direction of 180°), that is, a case where $\alpha$ is 0°. In this case, when a concave mirror is arranged so that $\alpha$ is 0° based on the first principle, an image reflected by the concave mirror toward the lens 5 is superposed on a real sample, and therefore, the image cannot be seen through the lens 5. Therefore, as shown in FIG. 3A, the concave mirror is arranged at another position M1 so that, as in the case shown in FIG. 2, a real image of a point P on the sample S is formed at a point Q on a real image S1 of the sample S, and both the real sample S and the real image S1 are picked up by the camera 4 arranged above the sample S. However, the case shown in FIG. 3A is different from the case shown in FIG. 2 only in that the real image S1 is formed by reflection by the concave mirror M1 and the two bending mirrors M5 and M6. The formation of the real image S1 using the two bending mirrors M5 and M6 will be explained in an easily understood manner using virtual images S' and S1' intermediately formed. The virtual image S' is a virtual image of the sample S formed by the "bending mirror M5", and the virtual image S1' is a virtual image of the finally-formed real image S1 formed by the "bending mirror M6". Similarly, P' is a virtual image of the attention point P on the sample S formed by the "bending mirror M5", and Q' is a virtual image of "Q that is a conjugate point of P" formed by the "bending mirror M6".

FIG. 3B is a partial view taken from FIG. 3A, which shows only the virtual images S' and S1' and parts relating to the concave mirror M1. The formation of real image Q of P will be described with reference to FIGS. 3A and 3B. First, referring to FIG. 3A, the sample S and the attention point P on the sample S are transferred by the "bending mirror M5" to S' and P', respectively. Then, referring to FIG. 3B, the S' and P' are transferred by the concave mirror M1 to S1' and Q'. It is to be noted that C1 is a center of curvature of the concave mirror M1, and R is a radius of curvature of the concave mirror M1. As has been described above with reference to the first principle, also in this case, the virtual images P' and Q' are formed symmetrical to each other with respect to the point C1. Referring FIG. 3A again, the S1' and Q' are finally transferred by the "bending mirror M6" to S1 and Q.

In this way, an image of the sample S inverted relative to the camera (which refers to a combination of the lens 5 and the CCD4) is formed at the position S1. Therefore, it is only necessary for the camera to pick up the real sample S and the inverted image S1 formed next to the sample S in the usual manner.

The second principle can be summarized as follows. The use of two or more plane mirrors together with a concave mirror makes it possible to form a real image of the sample S observed from a desired direction at a position adjacent to the sample S and, in addition, to allow light from the image to travel toward the main imaging lens 5 so that the image is finally formed at a desired position on the CCD 4.

The significance of "forming a real image of a sample within a substantial focus range of the main imaging lens while allowing light beams from the real image to travel toward the main imaging lens" and the definition of the "substantial focus range" will be described below.

The means for solving the problem described above in detail can be summarized in the following two points.

1) In each of the optical waveguide paths provided in different directions other than an optical waveguide path for direct observation of a sample through a camera, a real image of the sample is once formed at some point so that the real image and the sample are at substantially the same distance from the main imaging lens, and the real images observed from different directions are simultaneously picked up by the main imaging lens.

2) Even when a real image is formed, a desired image can be formed on the CCD only by allowing light beams from the real image to travel toward the main imaging lens. Therefore, light beams from the real image are allowed to travel toward the main imaging lens by appropriately selecting the size and position of a concave mirror and, if necessary, using a plane mirror together with a concave mirror.

Here, when "a real image of a sample is formed at substantially the same distance as the sample from the main imaging lens", a tolerance for "substantially the same distance as the sample" is determined in the following manner. A tolerance for the displacement δL (mm) of a real image is determined according to the amount of lateral blur δY (mm) resulting from δL. The amount of blur δY, which is generally used to determine the depth of focus of a camera lens, satisfies the relationship represented by the formula, $$\delta Y/D = \delta L/L \quad (2),$$

wherein δL is the amount of displacement, D (mm) is the actual aperture of the main imaging lens, and L (mm) is the distance between the main imaging lens and the real image (see FIG. 15). The value of δY is a desired positional resolution of an image which depends on the purpose of measurement, and is therefore a given value assumed to be, for example, 0.5 mm or 1 mm. Therefore, a tolerance for displacement δL can be determined by the formula, $$\delta L = (L/D)\delta Y \quad (3).$$

For example, in a case where δY is assumed to be 1 mm and L is 300 mm, when the main imaging lens is a large-aperture lens (D=50 mm), δL is 6 mm, when the main imaging lens is a medium-aperture lens (D=20 mm), δL is 15 mm, and when the main imaging lens is a small-aperture lens (D=2 mm), δL is 150 mm. As can be seen from this example, when the main imaging lens has a larger aperture for higher sensitivity, the need to once form a real image in a small length range on the optical waveguide path is higher. The above-described δL is a tolerance for "substantially the same distance as a sample". The "substantial focus range" of the main imaging lens is defined as a range of ±δL along the back-and-forth direction of the focal point of the main imaging lens, that is, a range having a length of 2δL. As described above, the range having a length of 2δL varies depending on a target positional resolution δY and the aperture of the main imaging lens. However, the above definition makes it possible to clarify the requirement of the present invention, that is, the significance of "forming a real image of a sample in a specified optical waveguide path within a substantial focus range of the main imaging lens while allowing light beams from the real image to travel toward the main imaging lens".

It is to be noted that a concave mirror is most practically useful as the optical element for forming a real image of a sample within a substantial focus range of the main imaging lens, but a combination of a plane mirror and a convex lens may also be used. In the case of this variation, two functions of a concave mirror are separately performed by the plane mirror and the convex lens. That is, the plane mirror is responsible for bending of an optical path and the convex mirror is responsible for formation of a real image of a sample.

In some embodiments of the present invention which will be described later, the first principle and the second principle are utilized in combination to form images of the sample S observed from two or more directions on the two-dimensional detector such as a CCD.

It is to be noted that Patent Document 2 discloses an embodiment using a concave mirror as a back-side mirror instead of a plurality of plane mirrors. However, this embodiment disclosed in Patent Document 2 is the same as the present invention in that a concave mirror is used, but is completely different in the usage of a concave mirror. The difference will be described below in detail.

As can be seen from a comparison between FIG. 10 and FIG. 3 of Patent Document 2, in FIG. 10, the three plane mirrors shown in FIG. 3 are replaced with one concave mirror. This indicates that in Patent Document 2, a concave mirror is regarded as equal to a combination of a plurality of small plane mirrors. Further, as shown in FIG. 10, points on the concave mirror correspond to different directions and are projected onto a detector in order. That is, in the case shown in FIG. 10 in Patent Document 2, only one concave mirror is used to form one image of a sample viewed from various directions.

On the other hand, in the present invention, a concave mirror is provided in each of the optical waveguide path provided in different directions so that an image of a sample is once formed in each of the optical waveguide paths at substantially the same distance as the sample from the main imaging lens. This makes it possible to arrange the sample and its images at the same distance from the lens. As will be described later with reference to some embodiments in detail, a real image of a sample observed from one direction is formed by one concave mirror, and therefore, in the case shown in FIG. 1 of the present invention, two real images observed from two different directions are formed by two concave mirrors, and thus, a total of three images including a direct image are formed. Similarly, in the case shown in FIG. 4A of the present invention, four real images observed from four different directions are formed by four concave mirrors, and thus, a total of five images including a direct image are formed. As described above, the Patent Document 2 and the present invention are completely different from each other in the usage of a concave mirror.

(Function)

Light beams emitted from a sample in two or more directions are guided by optical waveguide paths provided in the two or more directions directly or by reflection by an optical element to different positions on the common two-dimensional detector. The optical element for reflecting light has the function of guiding light traveling in an optical waveguide path including the optical element to a position at an appropriate distance from a direct image of a sample on a common detector. As shown in FIG. 16A, depending on the type of optical element (e.g., a plane mirror), defocusing occurs due to a difference in optical path length from direction to direction, which results in the necessity to provide an auxiliary lens. However, according to the present invention, a real image of a sample is formed at the same distance as the sample from the main imaging lens, that is, at a distance equal to the focal length of the main imaging lens by utilizing the imaging ability of an optical element. This eliminates the necessity to provide an auxiliary lens or the like between the sample and the main imaging lens for focus correction, which is the greatest advantage of the present invention.

Further, according to the present invention, a cheap spherical concave lens is unexpectedly suitable for obtaining such an advantage and astigmatism of a spherical mirror can be reduced by taking some measures. These two additional two remarkable points of the present invention will be supplementarily described below.

As described above to some extent with reference to the second principle, the first remarkable point is that a spherical concave mirror is particularly suitable for 1:1 imaging. It is well known that light emitted from one focal point of an ellipsoidal mirror converges to the other focal point. A spherical mirror can be regarded as a variation of an ellipsoidal mirror where the two focal points are at the same position, and therefore, it is natural that light emitted from the center of curvature C of a spherical mirror is focused on the point C without aberration. It can be expected from the fact that a clearer image can be obtained when the imaging magnification is closer to 1 and the distance between the center of curvature C and each of a pair of the point P on the sample and the point Q on the image of the sample is smaller.

FIG. 12 shows a comparison of spot diagrams obtained by calculating aberration at magnifications of 1:0.5 (top), 1:1 (middle), and 1:2 (bottom), assuming that an image of the point P is formed by a concave mirror on the point Q. As can be seen from FIG. 12, 1:1 imaging using a spherical concave mirror is particularly advantageous. In the five spot diagrams in each case, the central spot diagram (marked with a circle) is at the best imaging position and the other four spot diagrams are at positions shifted back and forth from the focal point by a certain amount (mm). It is to be noted that aberration was calculated under the conditions where the R (radius of curvature) of the concave mirror was 150 mm, the diameter of a beam of light impinging on the concave mirror was 24 mm, and the angle ∠PGR was 2°. The scale bar on the left side equals 0.05 mm and represents the spot size.

As can be seen easily from a comparison of the central spot diagrams marked with a circle, 1:1 imaging is advantageous as expected.

The second remarkable point relates to astigmatic aberration. Astigmatic aberration is usually explained using such a diagram as shown in FIG. 13. Assuming that the point G is the center of a circular beam of light impinging on the concave mirror and the point PGR are present in a horizontal plane, light emitted from the point Q located at a distance of R (radius of curvature) from the point G is reflected by the concave mirror and the reflected light traveling in a horizontal plane is focused on the point P1 slightly in front of the target point P on which light should be focused, and therefore, light intensity at the point P1 is distributed along a vertical line as shown in FIG. 13. On the other hand, the reflected light traveling in a vertical plane is focused on the point P2 slightly behind the point P, and therefore, light intensity at the point P2 is distributed along a horizontal line. The point P intermediate between the point P1 and the point P2 is at a distance of R from the point G. Light intensity at the point P, on which light should be focused, is distributed in a circular pattern, but the diameter of a circular beam at the point P increases as the distance between the point P1 and the point P2 increases. Therefore, the distance between the point P1 and the point P2 (axial astigmatism) is preferably smaller.

Axial astigmatism can be determined using the following formulas.

The point P1 is in front of the point P, on which light should be focused, and therefore, the distance between the point G and the point P1 can be approximately determined by the formula, $$GP_1 = 2R \cos(\beta/2) \qquad (4)$$

The point P2 is behind the point P, on which light should be focused, and therefore, the distance between the point G and the point P2 can be approximately determined by the formula, $$GP_2 = 2R\left(\frac{1}{\cos(\beta/2)}\right) \qquad (5)$$

Therefore, the distance between the point P1 and the point P2 (axial astigmatism) can be determined as the difference between GP1 and GP2, and is therefore represented by the formula, $$P_1 P_2 = 2R\left(\frac{1}{\cos(\beta/2)} - \cos(\beta/2)\right) \qquad (6)$$

Further, the point P is located substantially midway between the point P1 and the point P2, and therefore, the distance between the point P and the point P1 can be approximately determined by the formula, $$P_1 P = 2R(1 - \cos(\beta/2)) \qquad (7)$$

Calculation was performed using the formula (7) by changing the value of β. The relationship between axial astigmatism and the angle β when the radius of curvature R is 150 mm or 300 mm is shown in Table 1.

TABLE 1

| β (degrees) | Distance between P1 and P2 (Radius of curvature of concave mirror: 150 mm) |
|---|---|
| 5 | 0.57 |
| 10 | 2.29 |
| 15 | 5.16 |
| 20 | 9.19 |
| 25 | 14.40 |
| 30 | 20.81 |

| β (degrees) | Distance between P1 and P2 (Radius of curvature of concave mirror: 300 mm) |
|---|---|
| 2.5 | 029 |
| 5 | 1.14 |
| 7.5 | 2.57 |
| 10 | 4.58 |
| 12.5 | 7.15 |
| 15 | 10.31 |

The angle β is determined by the ratio between the distance between the sample and each of the conjugate points (P and Q) of its image and the radius of curvature R of the concave mirror. Therefore, when P and Q are given, the angle β can be reduced by increasing the radius of curvature R. In view of the fact that the angle β can be reduced to half by doubling the radius of curvature R, in the calculation shown in Table 1, the angle β when the radius of curvature R was 300 mm was reduced to half that when the radius of curvature R was 150 mm.

As shown in Table 1, the distance between the P1 and P2 (astigmatic aberration) is rapidly increased (in proportion to not β but substantially the square of β) by increasing the angle β. As can be seen from the result, when the radius of curvature R is doubled, the angle β is reduced to half while the distance between P1 and P2 is reduced in proportional to substantially the square of β (i.e., ¼), and therefore, astigmatic aberration is reduced to half (i.e., 2×(¼)).

As has been described above, in order to create a clear image, it is important that the angle β (i.e., the angle formed by PGQ) is minimized. That is, it is important to arrange a concave mirror so that the angle β can be minimized, and therefore, it can be said that a key design point is to devise an arrangement of the auxiliary plane mirror M5, M6, or the like to minimize the angle β. In the above embodiments, concave mirrors are arranged so that such a requirement can be satisfied as far as possible.

Further, when the entire image of a larger sample is observed, the point Q is farther from the point P, and therefore the edge of the image is slightly out of focus and the central portion of the image is in focus because the angle QGP is small. Further, it is also possible to take some measures to increase the radius of curvature (i.e., to decrease the angle β). In this case, reflection by a plane mirror may be utilized to save space.

According to the present invention, it is possible to achieve the following.

1) As has been described above with reference to the first principle and the second principle, it is not necessary to provide an auxiliary lens in at least one optical waveguide path just before the main imaging lens. This makes it possible to perform multi-directional simultaneous observation using a large-aperture main imaging lens, which is particularly advantageous in that multi-directional luminescence measurement requiring a bright optical system can be performed with high sensitivity.

2) The images of a sample formed in optical waveguide paths are at the same distance from the main imaging lens. This makes it possible to solve the problem that the back-side image of the sample is small in size (due to the formation of a virtual image at a position far from the sample).

3) It is not necessary to provide any optical parts such as auxiliary lenses between the sample and the main imaging lens. This makes it possible to simplify the structure of the biological imaging device according to the present invention.

4) The following two additional advantages resulting from the effect 3) described above can be obtained.

(4-1) The number of observation directions for simultaneous observation can be selected by changing the distance between the main imaging lens and the sample.

(4-2) Selection between two observation modes (i.e., one-directional observation of two or more samples and multi-directional observation of one sample) can be easily performed.

These effects can be summarized as follows. The additional effects 2) and 4) can be incidentally obtained by achieving the object of the present invention, that is, by achieving a bright optical system capable of guiding light beams emitted from a sample in various directions to different positions on a two-dimensional detector to simultaneously measure the sample from various directions.

It is to be noted that it is not always necessary to form a real image of a sample at some point in all the optical waveguide paths. That is, sufficient effect can be obtained also when the first principle of the present invention is applied to only an optical waveguide path in which the distance between a virtual image and the main imaging lens is greatly different from the distance between an image and the main imaging lens in other optical waveguide path. For example, in the following second embodiment, some of optical waveguide paths use not a real image but a virtual image and only the other optical waveguide paths use a real image. Further, the first and second principles have been described above with reference to a typical case where images guided by an "optical waveguide path receiving direct light from a sample" and an "optical waveguide path not receiving direct light from a sample" are simultaneously picked up by the main imaging lens, but the present invention can be achieved even when an "optical waveguide path receiving direct light from a sample" is not provided, which will be described later with reference to a seventh embodiment.

Prior to a description of various embodiments of the present invention, the optical waveguide path as a main part of the present invention is classified into three types and summarized in FIG. 17 to further clarify the concept of the optical waveguide path. The following embodiments include all or some of the three types of optical waveguide paths shown in FIG. 17.

In FIG. 17, optical elements, such as reflection mirrors and lenses, which should be provided to reflect light beams are not shown for the sake of simplicity to emphasize only optical waveguide paths and light beams traveling in the optical waveguide paths. In FIG. 17, the symbol "S" represents a sample, the reference numeral 5 represents a main imaging lens, and the reference numeral 4 represents a two-dimensional detector.

An optical waveguide path 102 is an "optical waveguide path receiving direct light from a sample", and this type of optical waveguide path is defined as a Type 1 optical waveguide path.

Optical waveguide paths 104, 104A, and 106 are all "optical waveguide paths not receiving direct light from a sample". Among these optical waveguide paths, each of the optical waveguide paths 104 and 104A is an optical waveguide path in which a real image of the sample S is formed at a position S1 or a position S2. This type of optical waveguide path is defined as a Type 2 optical waveguide path. That is, the Type 2 optical waveguide path is an optical waveguide path not receiving direct light from a sample and forming a real image. The reason why the two types of Type 2 optical waveguide paths 104 and 104A are shown is to indicate that focusing may be performed twice or more in the optical waveguide path forming a real image as long as a finally-formed image is within a focal point range of the main imaging lens. More specifically, in the optical waveguide path 104, a real image is formed only once, but in the optical waveguide path 104A, a real image is formed twice and a real image S2 formed later (second real image) is located within a focal point range of the main imaging lens so that the real image S2 and images guided by other optical waveguide paths are formed on the two-dimensional detector.

The optical waveguide path 106 is an optical waveguide path in which not a real image but a virtual image (S3) is formed, and this type of optical waveguide path is defined as a Type 3 optical waveguide path. That is, the Type 3 optical waveguide path is an "optical waveguide path not receiving direct light from a sample and not forming a real image".

It is to be noted that in FIG. 17, in order to explain the mechanism of image formation in the optical waveguide path, how two light beams passing through the ends of the main imaging lens 5 among a plurality of light beams emitted from each of four attention points P1, P2, P3, and P4 on the sample S travel in each of the optical waveguide paths is shown. The two Light beams emitted from the point P1 and traveling in the optical waveguide path 102 directly enter the lens 5 and pass through both ends of the lens 5, and are then focused on the two-dimensional detector. The two light beams emitted from the point P2 and traveling in the optical waveguide path 104A are focused on Q2' and Q2 (twice in total), and travel toward the main imaging lens 5, and are focused on the two-dimensional detector. The two light beams emitted from the point P3 and traveling in the optical waveguide path 104 are focused on Q3 (only once), and pass through the main imaging lens 5, and are focused on the two-dimensional detector. The two light beams emitted from the point P4 and traveling in the optical waveguide path 106 travel as if they were emitted from a virtual image Q4, and enter the main imaging lens 5, and are focused on the two-dimensional detector.

As has been described above, the present invention cannot be achieved only by the Type 1 optical waveguide path and/or the Type 3 optical waveguide path. A requirement to achieve the present invention is to provide at least one Type 2 optical waveguide path.

As has been described above in detail with reference to FIG. 16C, in the case of a Type 3 optical waveguide path forming a virtual image in which light emitted from the back side of a sample is reflected toward the detector, the virtual image is formed at a distance from the sample and outside a focal point range of the main imaging lens 5. In this case, the virtual image can be forcibly shifted into the focal point range only by providing an auxiliary lens near the main imaging lens, but this has the disadvantage that the auxiliary lens overlaps with other optical waveguide paths.

It is to be noted that in FIG. 17, the Type 1 optical waveguide path is slightly displaced from the center of symmetry by design. The reason for this is as follows. In many of the following embodiments, an "optical waveguide path receiving direct light from a sample" is arranged along the center of symmetry, which is not a requirement to achieve the present invention but a requirement limited to each individual embodiment.

BRIEF DESCRIPTION OF THE DRAWINGS

FIG. 1C is a schematic front sectional view (FIG. 1B) showing optical waveguide paths.

FIG. 8A is a schematic front sectional view showing a fourth embodiment capable of changing the number of observation directions, which is in a five-directional measurement mode.

FIG. 11B is a schematic front sectional view of the sixth embodiment, wherein the centers of curvature of the concave mirrors are moved away from the sample.

FIG. 16A is a diagram of a multi-faceted mirror system regarded as a biological imaging device, which is used for explaining a schematic structure for acquiring images of a sample observed from obliquely below and the function of an auxiliary lens for correcting the distance between images.

DESCRIPTION OF THE REFERENCE NUMERALS

4 CCD
5 main imaging lens
M1 to M6 concave mirrors or plane mirrors

DETAILED DESCRIPTION OF THE INVENTION

First Embodiment

Optical System for Simultaneous Observation from Five Directions

Figure 4A:
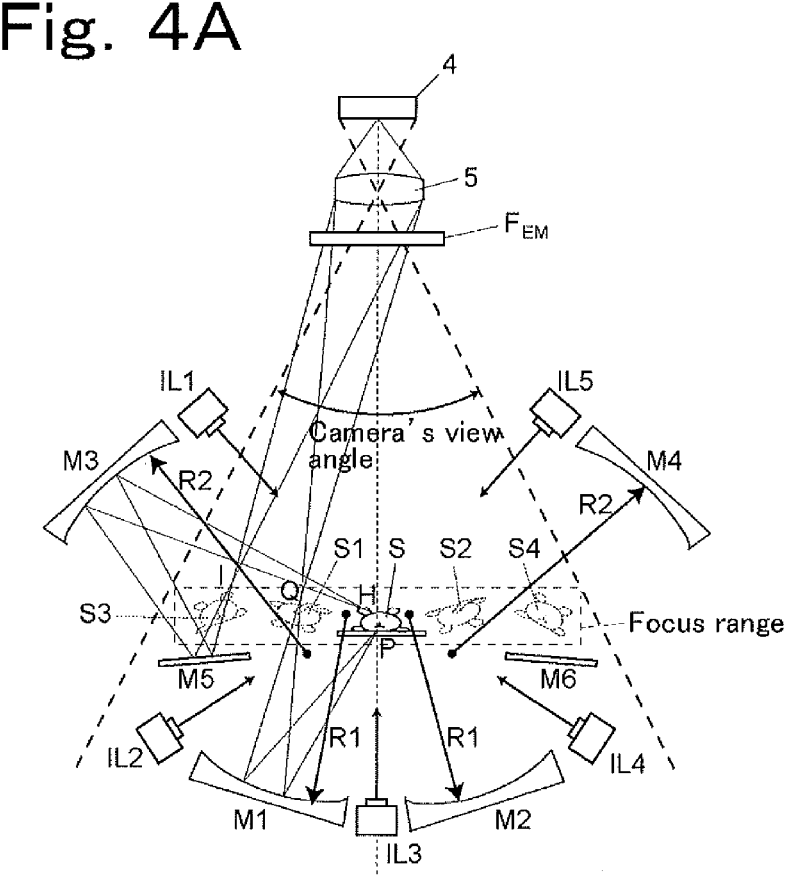
FIG. 4A is a schematic front sectional view of a first embodiment for picking up images of a sample observed from five directions.
Figure 4B:
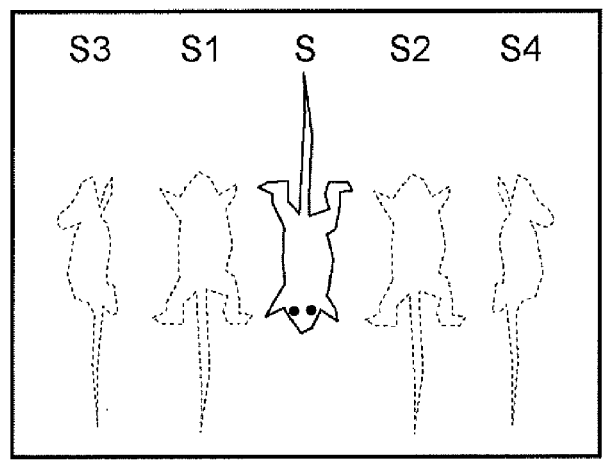
FIG. 4B is a plan view showing images picked up by the first embodiment.

Hereinbelow, an optical system for simultaneous observation from five directions will be described by way of example with reference to FIGS. 4A and 4B. As shown in FIG. 4A, a sample S is placed in the center of the optical system, and a main imaging lens 5 and a CCD 4 are arranged directly above the sample S (in a direction corresponding to an observation angle of 0°), and four concave mirrors M3, M1, M2, and M4 are arranged in directions corresponding to observation angles of 60°, 135°, 205°, and 300°, respectively. That is, an optical waveguide path in the direction of 0° provides a region occupied by light traveling directly from the sample S to the lens 5, an optical waveguide path in the direction of 60° provides a region occupied by light traveling from the sample S through the concave mirror M3 and a plane mirror M5 to the lens 5, an optical waveguide path in the direction of 135° provides a region occupied by light traveling from the sample S through the concave lens M1 to the lens 5, an optical waveguide path in the direction of 205° provides a region occupied by light traveling from the sample S trough the concave mirror M2 to the lens 5, and an optical waveguide path in the direction of 300° provides a region occupied by light traveling from the sample S through the concave mirror M4 and a plane mirror M6 to the lens 5. In the optical waveguide paths in the directions of 135° and 205° out of these optical waveguide paths, real images of the sample S are once formed by the concave mirrors M1 and M2 at positions S1 and S2 based on the above-described first principle, and then light from each of the real images travels toward the main imaging lens 5 and is again focused by the lens 5 on the CCD 4. Further, in the optical waveguide paths in the directions of 60° and 300°, real images of the sample S are formed at positions S3 and S4 by the concave mirrors M3 and M4 arranged obliquely above the sample S. This is based on the above-described second principle, that is, the traveling direction of light from the real image and the position of the real image are changed to a desired direction and a desired position, respectively, by the function of the bending mirror M5 or M6.

As can be seen from FIG. 4A, light emitted from an attention point P located on the lower side of the sample S is once focused by the concave mirror M1 on a point Q on the real image S1 and is then again focused by the main imaging lens 5 on the two-dimensional detector 4, and further, light emitted from an attention point H located on the upper side of the sample S is reflected by the concave mirror M3 and the bending mirror M5 and is once focused on a point I on the real image S3, and is then again focused by the lens 5 on the two-dimensional detector 4.

These four real images S1 to S4 and the sample S are at a similar distance from the lens 5 at which the lens 5 can properly focus, and therefore, a total of five images including a direct image of the sample S and the four real images can be simultaneously formed on the CCD 4 and picked up. As a result, as shown in FIG. 4B, the five images of the sample S observed from different five directions are formed on the CCD 4 in the following order, from left to right, S3 (observation direction: 50°), S1 (observation direction: 135°), S (observation direction: 0°), S2 (observation direction: 205°), and S4 (observation direction: 300°). It is to be noted that only in the central image the direction of the mouse head is opposite to other images.

Figure 16B:
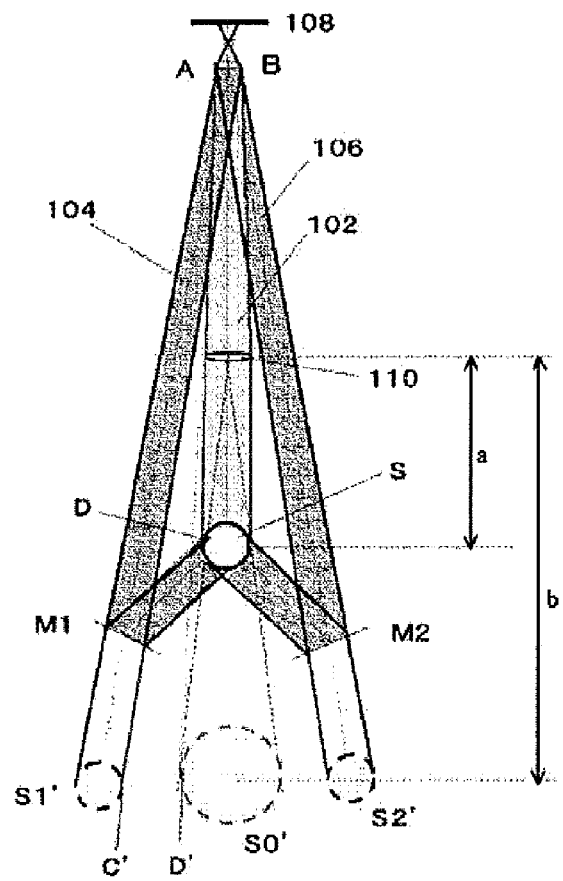
FIG. 16B is a diagram of a multi-faceted mirror system regarded as a biological imaging device for explaining overlapping between optical waveguide paths at the position of an auxiliary lens when the aperture of a main imaging lens is small.
Figure 16C:
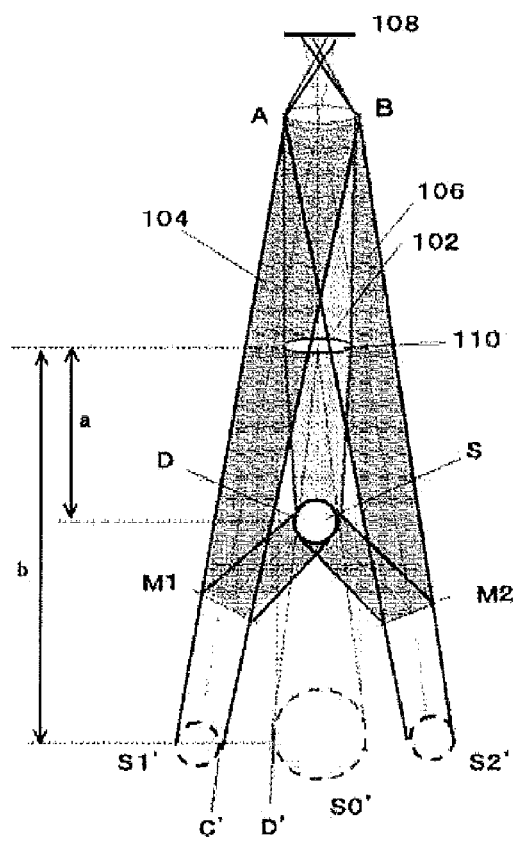
FIG. 16C is a diagram of a multi-faceted mirror system regarded as a biological imaging device for explaining overlapping between optical waveguide paths at the position of an auxiliary lens when the aperture of a main imaging lens is large.

The feature of this five-directional optical observation system is that it does not need to have any optical parts, such as focusing auxiliary lenses between a sample and a camera (in this case, a combination of the lens 5 and the CCD4), and therefore, overlapping of the five optical waveguide paths with one another near the main imaging lens 5 does not cause any problem and the main imaging lens 5 can have a large aperture. That is, the problems described above with reference to FIG. 16 can be solved, which makes it possible to achieve the original intention of the present invention, i.e., it is possible to achieve a bright observation system capable of simultaneously forming two or more images observed from different directions on the common CCD 4 without providing any movable parts.

<Additional Description about Application of First Embodiment to Fluorescence Measurement>

The above description applies to a chemiluminescence mode or a bioluminescence mode in which molecular probes present in a sample emit light. Hereinbelow, the application of the optical system according to the first embodiment to a fluorescence mode in which molecular probes emit fluorescence by irradiation with excitation light will be described. Illumination light source units IL1, IL2, IL3, IL4, and IL5 ("IL" is an abbreviation for "illumination") are provided at five positions, and an excitation light source included in each of the light source units illuminates the sample S so that fluorescence is emitted from the sample S. The sample S is observed from five directions to form fluorescence images on the CCD 4, and the fluorescence images are picked up. It is to be noted that a fluorescence (excitation light cut-off) filter $F_{EM}$ may be inserted in front of the main imaging lens 5. By inserting the excitation light cut-off filter $F_{EM}$ during fluorescence measurement, it is possible to cut off an excitation wavelength component to form images containing only fluorescence on the CCD.

Figure 5A:
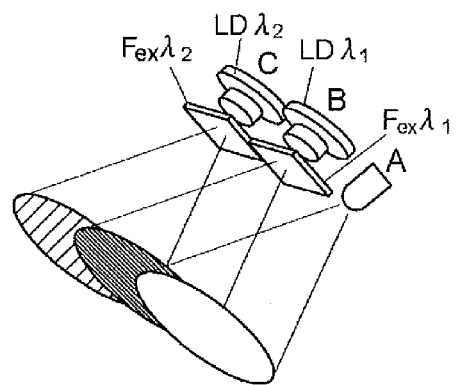
FIG. 5A is a schematic perspective view of an example of an illumination light source unit for use in a biological imaging device according to the present invention.

A specific example of the structure of each of the illumination light source units is shown in FIG. 5A. As shown in FIG. 5A, each of the illumination light source units includes different three types of light sources A, B, and C. As will be described later, the light source A is a white LED for illuminating a biological sample 4 to pick up photographic images of the biological sample 4. The light sources B and C are excitation light sources. More specifically, the light source B includes a laser diode (hereinafter, abbreviated as "LD") as a light-emitting device LDλ1 that emits excitation light having a wavelength of λ1 and an excitation interference filter $F_{ex}λ1$ attached to the light-emitting side of the light-emitting device LDλ1. The light source C includes a LD as a light-emitting device LDλ2 that emits excitation light having a wavelength of λ2 and an excitation interference filter $F_{ex}λ2$ attached to the light-emitting side of the light-emitting device LDλ2. If necessary, each of the light sources B and C may further have a diverging lens (not shown) attached to the light-output side of the interference filter $F_{ex}λ1$ or $F_{ex}λ2$ to irradiate the entire biological sample with light. The selection among the three types of light sources A, B, and C shown in FIG. 5A can be performed simply by turning on/off each of them without mechanical switching. Therefore, the direction of irradiation (IL1, IL2, IL3, IL4, or IL5) and the type of light source (A, B, or C) are selected, without mechanical switching, by turning on/off each of the light sources A, B, and C of each of the light source units IL1, IL2, IL3, IL4, and IL5 arranged in different irradiation directions.

Figure 5B:
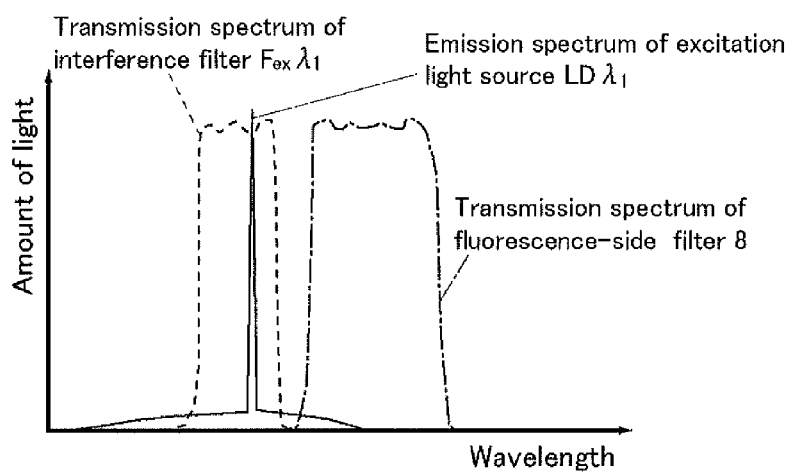
FIG. 5B is a spectrum diagram showing examples of characteristics of an excitation light source and an excitation interference filter included in the illumination light source unit shown in FIG. 5A.

Hereinbelow, the characteristics of the excitation light source and the characteristics of the excitation interference filter will be described with reference to FIG. 5B. FIG. 5B shows the relationship between the light-emitting device LDλ1 of the light source B and the interference filter $F_{ex}λ1$ attached to the light-emitting side of the light-emitting device LDλ1. The light-emitting device LDλ1 tends to be considered as a device that emits light of single wavelength λ1, but in fact, emits also weak light represented as a skirt portion of its emission spectrum. The skirt portion contains a wavelength component that passes through the fluorescence filter $F_{EM}$ provided as an excitation light cut-off filter on the light-input side of the two-dimensional detector CCD 4. Therefore, if a biological sample is irradiated with light containing such a wavelength component, such a wavelength component as well as a fluorescence component emitted from the biological sample passes through the fluorescence filter $F_{EM}$ and enters the two-dimensional detector 4. As a result, stray light, which is derived from a leak light component, other than fluorescence emitted from the sample appears in fluorescence images picked up by the two-dimensional detector 4, which reduces the sensitivity of detection for fluorescence.

However, in this embodiment, since the excitation interference filter $F_{ex}λ1$, which cuts off light represented as a skirt portion of the emission spectrum of the light-emitting device LDλ1, is attached to the light-emitting side of the light-emitting device LDλ1 to remove an excitation light component within the pass band of the fluorescence filter $F_{EM}$ from light emitted from the light-emitting device LDλ1, only a fluorescence component emitted from a biological sample passes through the fluorescence filter $F_{EM}$, thereby preventing a reduction in the ability to detect fluorescence due to contamination of images picked up by the two-dimensional detector 4 with stray light.

It is to be noted that the excitation light source has been described above with reference to the light source B, but the light source C also has the same structure as the light source B.

When LDs or LEDs are used as the excitation light sources included in the illumination light source units IL2, IL3, IL4, and IL5, only necessary one or more excitation light sources can be freely turned on by switching on/off the electric circuit of each of the excitation light sources. Therefore, all the excitation light sources arranged in five different directions may be turned on to measure fluorescence, or only necessary excitation light sources may be selectively turned on to measure fluorescence images. This makes it possible to acquire not only the fluorescence images of a sample irradiated with excitation light from its front side but also the fluorescence images of the sample irradiated with excitation light from only its back or lateral side. Therefore, each of the five images of an animal observed from five directions has five variations different in the irradiation direction of excitation light, that is, 25 images can be acquired in total by performing exposure five times. By observing these 25 images, it is possible to estimate whether a light emission source is in a shallow position or a deep position in the body of the animal. This is because when a light emission source is in a shallow position, it is estimated that a small bright spot appears in a subject in any one of the 25 images, but on the other hand, when a light emission source is in a deep position, diffused light distribution is observed in all of the 25 images.

According to such an excitation method as described above, by simply turning on/off each of the excitation light sources, the irradiation direction of excitation light can be freely selected from among the front, back, and lateral directions of a sample without any movable parts. Therefore, even in a fluorescence mode, a sample can be irradiated with excitation light from various directions covering all around the sample, and therefore, multi-directional images of the sample can be easily acquired.

Although the fluorescence mode has been described above with reference to a case where a sample is irradiated with excitation light "from a distance", it may have a variation in which the illumination light source unit IL1 or the like is brought into contact with a sample during irradiation with excitation light. In this case, for example, a mouse is irradiated with excitation light by bringing two small illumination light source units into contact with the right and left sides of its abdomen. Such contact irradiation has the advantage that selective excitation of only a site of interest (e.g., an organ of interest) in a sample can be easily achieved, that is, excitation of sites other than a site of interest in a sample can be avoided. When a large area of a sample is irradiated with excitation light, autofluorescence, which interferes with measurement, is also inevitably generated in the sample. Contact irradiation is an excitation method in which importance is placed on the effect of avoiding autofluorescence. Also, in the case of contact irradiation, multi-directional observation can be performed, and therefore "contact excitation-type fluorescence observation images" observed from, for example, five directions can be acquired.

However, contact irradiation has the disadvantage that the illumination light source unit cuts off part of an observation image. Therefore, in a case where contact irradiation is selected, it is necessary to balance the "advantage obtained by selective excitation of a site of interest" against the "disadvantage caused by cutting off part of an image". The disadvantage of contact irradiation should be addressed by minimizing the size of illumination light source units for contact irradiation.

It is to be noted that among the light sources shown in FIG. 5A, the light source A is a white LED and is turned on when photographic images of a sample are picked up. In both cases of luminescence image measurement and fluorescence image measurement, photographic images of a sample illuminated with a white LED are acquired before or after fluorescence or luminescence measurement to determine which site in the sample emits light. This makes it possible to know where a light-emitting site is located in the photographic images of a sample by image analysis by superposing photographic image data on luminescence images or fluorescence images or by arranging photographic image data and luminescence images or fluorescence images so that a comparison can be made between them.

The above-described excitation light source and white light source are very important but are not main components of the present invention and are merely components used in the present invention. Therefore, the illumination light source units are shown for purpose of illustration only in FIG. 4A showing the first embodiment. In the following examples, description about the light sources will be omitted because it is only necessary to arrange the same light sources at desired positions around a sample so as not to overlap with reflection mirrors.

Further, the direction of observation and the direction of irradiation with light are independent of each other. Although the following examples will be described with reference to the cases of two-, three-, four-, and five-directional observations, the direction of irradiation is not always the same as the direction of observation and the number of irradiation directions is not always the same as the number of observation directions, either. Therefore, the structure of the biological imaging device according to the present invention can be freely designed by combining, for example, three-directional irradiation with two-directional observation, or four-directional irradiation with three-directional observation, or five-directional irradiation with five-directional observation.

Second Embodiment

A second embodiment is the same as the first embodiment for five-directional observation except that the two concave mirrors as means for acquiring "images viewed from obliquely above" are changed to plane mirrors. The second embodiment will be described with reference to FIG. 6. As shown in FIG. 6, plane mirrors M5 and M6 are arranged obliquely above the sample S instead of the concave mirrors for acquiring "images viewed from obliquely above" (M3 and M4 shown in FIG. 4A) to form virtual images S3 and S4, respectively. That is, among the five optical waveguide paths, the two optical waveguide paths in the directions in which the sample S is observed from obliquely above are changed to an optical waveguide path in which light travels from the sample S through the plane mirror M5 to the lens 5 and an optical waveguide path in which light travels from the sample S through the plane mirror M6 to the lens 5, but the other three optical waveguide paths in three different directions are the same as those of the first embodiment. Each of the optical waveguide paths for observation from obliquely above is bent by the plane mirror, and therefore, the optical path length thereof is slightly longer than that of the optical waveguide path in which light travels directly from the sample S to the lens 5. Therefore, the virtual images S3 and S4 formed by the plane mirrors M5 and M6, respectively, are slightly farther from the lens 5 than the real images S1 and S2 and the sample S. Unlike the first embodiment in which the sample S and the four real images S1, S2, S3, and S4 are ideally at the exact same distance from the lens 5, in the second embodiment, there is a difference in distance from the lens 5 between (S3, S4) and (S1, S, S2). However, since the difference is very small and at an acceptable level from a practical viewpoint, it is not necessary to provide an auxiliary lens in each of the optical waveguide paths for observation from obliquely above. That is, the plane mirrors are arranged so that the virtual images S3 and S4 can be formed in a substantial focus range of the lens 5 and light beams from the virtual images S3 and S4 can travel toward the lens 5.

The image formation using the optical system according to the second embodiment can be summarized as follows. In the optical waveguide path in the direction of 0°, light from the sample S directly enters the lens 5 and is focused by the lens 5 on the CCD 4. In the two optical waveguide paths for observation from obliquely above, light from the sample S is not focused midway, and the virtual images S3 and S4 are focused by the lens 5 on the CCD 4. Only in the two optical waveguide paths for observation from obliquely below, light from the sample S is once focused midway and is then again focused by the lens 5 on the CCD 4.

As described above, the second embodiment is an eclectic style using both a technique for forming a real image by a concave mirror and a technique for forming a virtual image by a plane mirror. However, it can be said that the second embodiment is advantageous from a practical viewpoint because adverse effects associated with forming virtual images "viewed from obliquely above" are weak, and the structure of the optical system can be made slightly simpler than that of ideal optical system according to the first embodiment. That is, it can be said that the second embodiment is an embodiment in which concave mirrors are provided only in optical waveguide path for observation from obliquely below so that light from a sample is focused midway in the optical waveguide path. This is because if a virtual image of a sample viewed from obliquely below is formed by a plane mirror, the virtual image is very far from the sample.

Figure 6A:
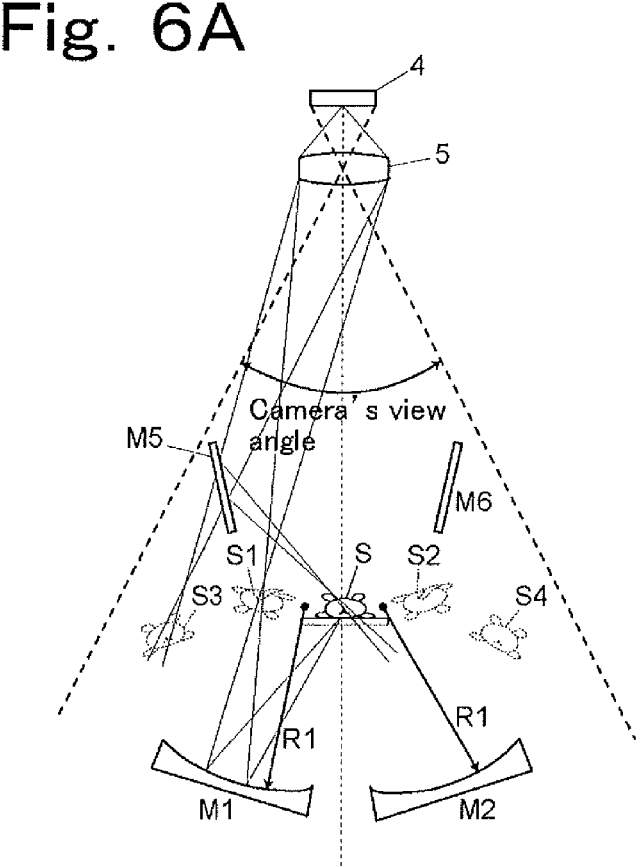
FIG. 6A is a schematic front sectional view of a second embodiment of the present invention for picking up images observed from five directions.
Figure 6B:
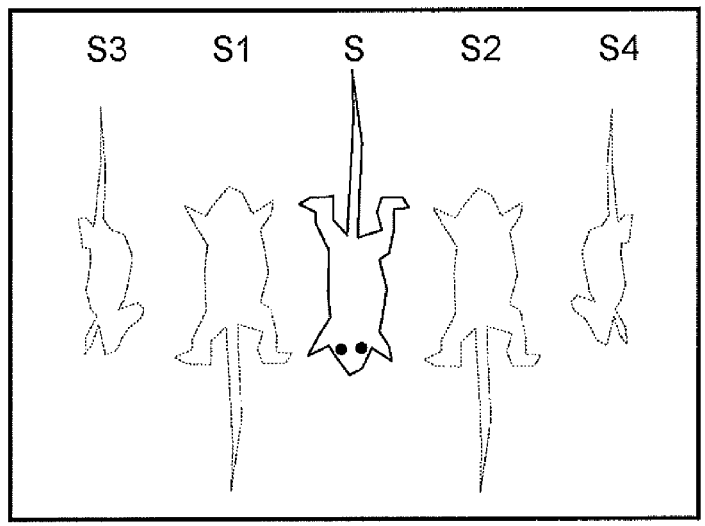
FIG. 6B is a plan view showing images picked up by the second embodiment.
Figure 6C:
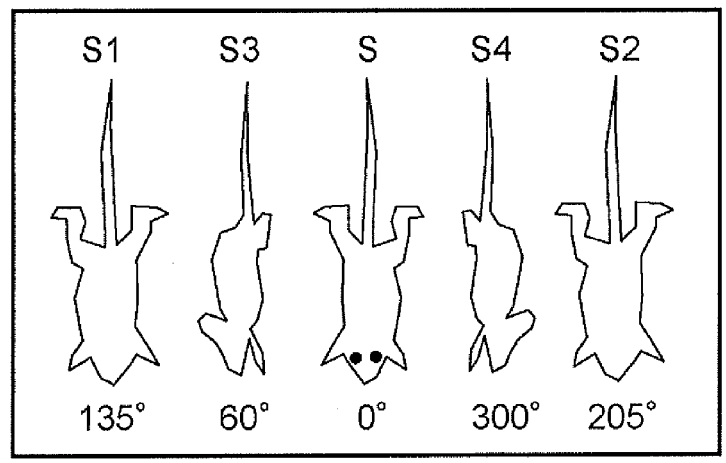
FIG. 6C is a plan view showing images obtained by converting the multi-directional images shown in FIG. 6B by an image converter.

FIG. 6B shows images formed on the CCD 4 in this embodiment. As shown in FIG. 6B, the leftmost image S3 and the rightmost image S4 are slightly smaller than those shown in FIG. 4B and are opposite in head-to-tail direction to those shown in FIG. 4B. However, such differences can be corrected by finally changing the display order and orientation of the images and adjusting the size of the images by appropriate image converting software. For example, as shown in FIG. 6E, the image converting software may be installed in an image converter 22 provided downstream of an image acquisition circuit 20 of the CCD 4 to convert the images shown in FIG. 6B to display converted images on a display 24 as shown in FIG. 6C. In this case, the image S1 (135°) and the image S2 (205°) are rotated 180° and the positions of the image S3 (60°) and the image S4 (300°) are changed so that all the images are oriented in the same direction and the images are arranged in consideration of the observation angle. Further, the image S3 (60°) and the image S4 (300°) are horizontally flipped and are enlarged.

Figure 6D:
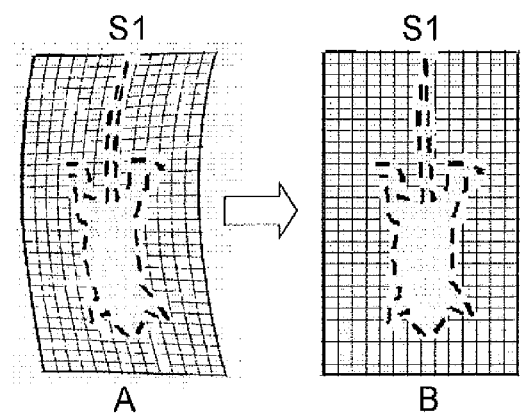
FIG. 6D is an illustration for explaining the correction of distortion of an image observed from one direction.
Figure 6E:
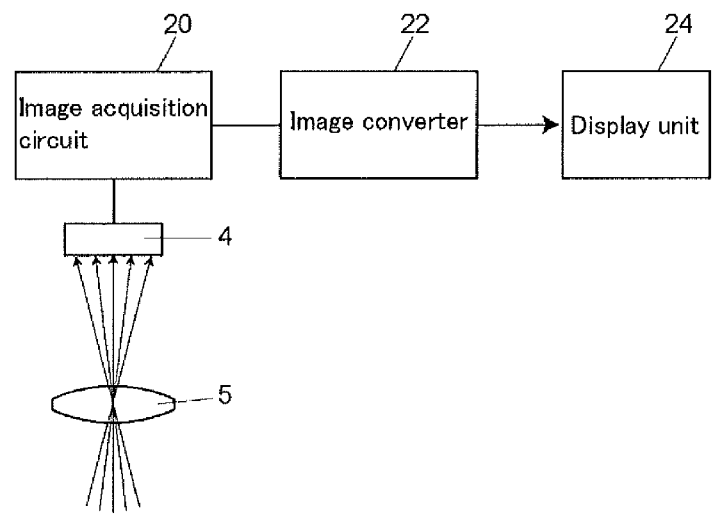
FIG. 6E is a block diagram showing an image acquisition circuit and an image converter provided downstream of a two-dimensional detector.

Further, as shown in FIG. 6D(A), there is a case where an image formed by a concave mirror undergoes distortion. That is, originally-straight lines are distorted by a concave mirror and are therefore observed as curves in a resultant image. However, the degree of distortion can be previously determined, and therefore, even when the image of a grid pattern formed by a concave mirror undergoes distortion as shown in FIG. 6D(A), the distortion can be corrected so that the lines of the grid pattern intersect at right angles as shown in FIG. 6D(B). For example, software for correcting distortion may be installed in the image converter 22. This makes it possible to perform distortion correction if necessary to display corrected images as shown in FIG. 6C. It is to be noted that it goes without saying that such image conversion as described above can be performed not only in the second embodiment but also in all the embodiments.

Third Embodiment

Figure 7A:
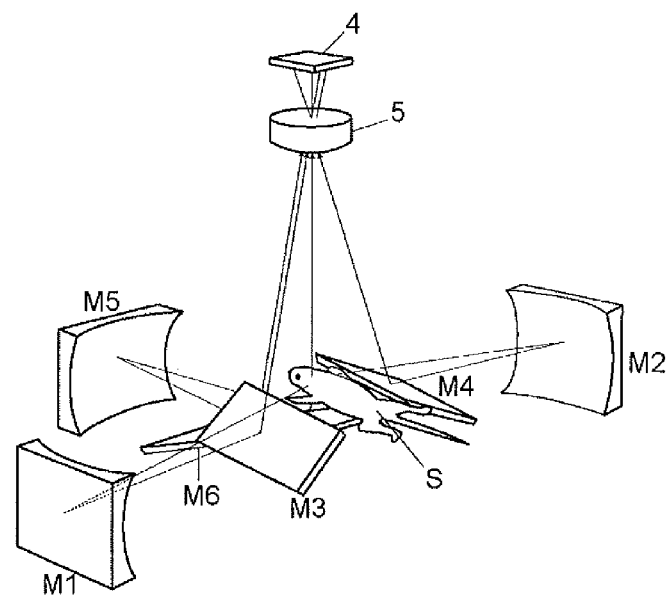
FIG. 7A is a schematic perspective view of a third embodiment for picking up images of a sample observed from four directions, i.e., from above, below, right, and left.

A third embodiment uses reflection mirrors in combination to measure not the entire body but part of a sample, for example, the head (brain) of a mouse as a sample from four directions (i.e., from above, below, right, and left). The third embodiment will be described with reference to FIGS. 7A to 7C.

Figure 2:
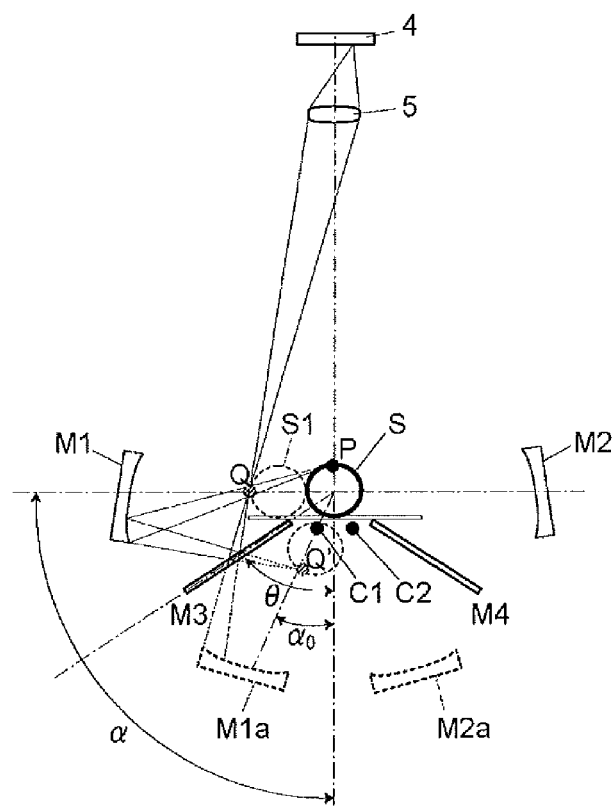
FIG. 2 is a schematic front sectional view for explaining a second principle of the present invention.

As in the cases of the first and second embodiments, the third embodiment also has the main imaging lens 5 and the CCD 4 arranged above the sample S. However, the third embodiment is different from the first and second embodiments in that the left-side image of the sample S is received by the concave mirror M1 and then reflected by the plane mirror M3 toward the lens 5 and the right-side image of the sample S is also received by the concave mirror M2 and is reflected by the plane mirror M4 toward the lens 5. This technique is a direct reflection of the second principle described above with reference to FIG. 2, and therefore, lateral images S2 and S3 of the sample S are formed on opposite sides of the sample S.

Figure 3A:
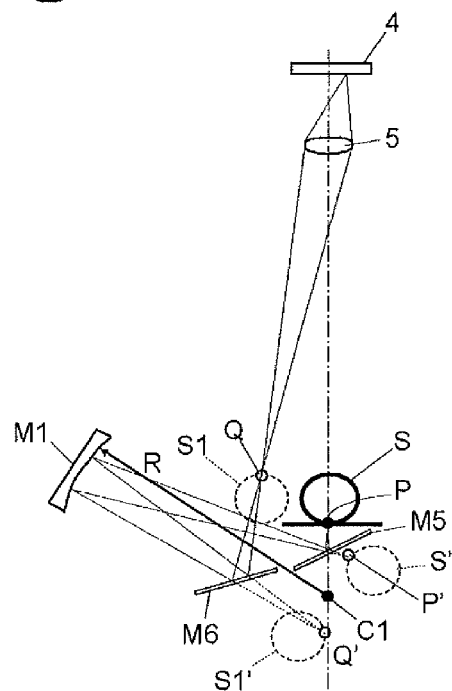
FIG. 3A is a schematic front sectional view for explaining a variation of the second principle of the present invention.
Figure 3B:
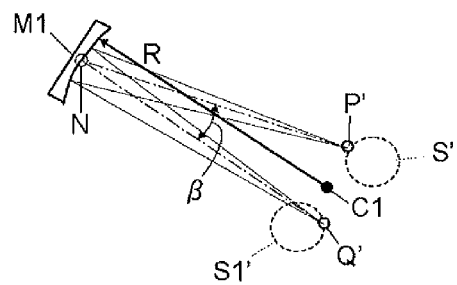
FIG. 3B is a partial view taken from FIG. 3A, which shows only a part relating to a concave mirror M1.

On the other hand, light traveling downward from the sample S is reflected by the plane mirror M6 toward the concave mirror M5, and the reflected light is again reflected by the plane mirror M6 upward toward the lens 5. The propagation path of light emitted downward from the sample S will be described with reference to FIG. 7C. A real image S3 of the sample S is formed by the concave mirror M5. The real image S3 and the sample S are symmetrical with respect to a center C5 (C5 is an image formed by the plane mirror M6) of the concave mirror M5 located at the tip of the head of the mouse as a sample. The image of an attention point P located on the lower side of the head of the mouse is formed at a point Q due to the concave mirror M5 and the twice reflections by the plane mirror M6, and can be observed as a back-side image of the sample from above. The principle on which the formation of a back-side image of the sample is founded is substantially the same as the variation of the second principle using bending mirrors described above with reference to FIGS. 3A and 3B. The difference is that the plane mirror M6 shown in FIG. 7C can be regarded as a combination of the plane mirror M5 and the plane mirror M6 shown in FIG. 3A. By providing two plane mirrors as shown in FIG. 3A, the angle of observation can be freely selected, and therefore, light from a sample traveling in the direction of 180° (i.e., directly below) can be directed toward the lens 5. However, in the case shown in FIG. 7C, the back side of the sample S is observed from a slightly oblique direction in exchange for simplification of the structure of the optical system due to the use of the common plane mirror.

Figure 7B:
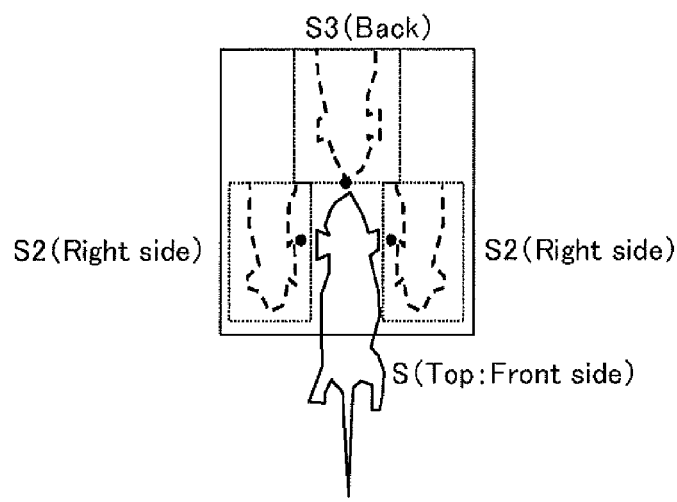
FIG. 7B is a plan view showing images picked up by the third embodiment.
Figure 7C:
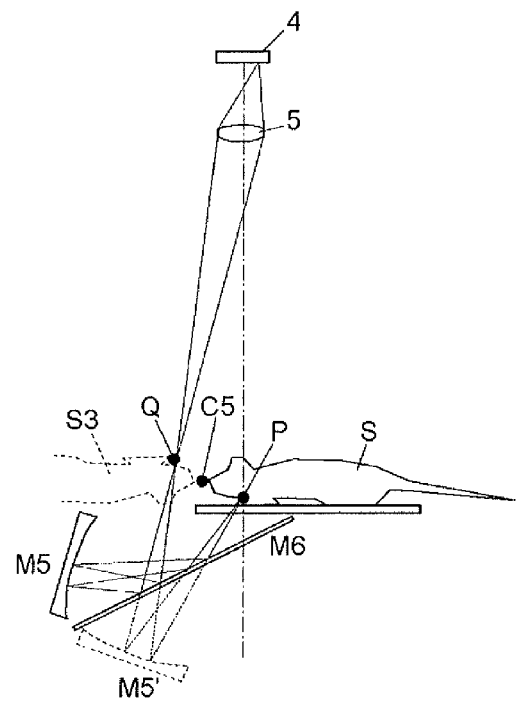
FIG. 7C is a schematic front sectional view for explaining the function of a plane mirror provided on the back side of the sample in the third embodiment.

In this way, four images including three left-side, right-side, and back-side images and a front (top)-side image are guided by four optical waveguide paths to the main imaging lens 5 and are formed on the CCD 4 as shown in FIG. 7B. In this embodiment, the target of observation is not the entire body of the sample S and is limited to part of the sample S, and therefore, the concave mirrors and the plane mirrors can be reduced in size.

Light traveling in the front direction is focused on the CCD only once, but light traveling in each of the other three directions is focused twice in total, once on some point in the optical waveguide path and once on the CCD.

Fourth Embodiment

Figure 8B:
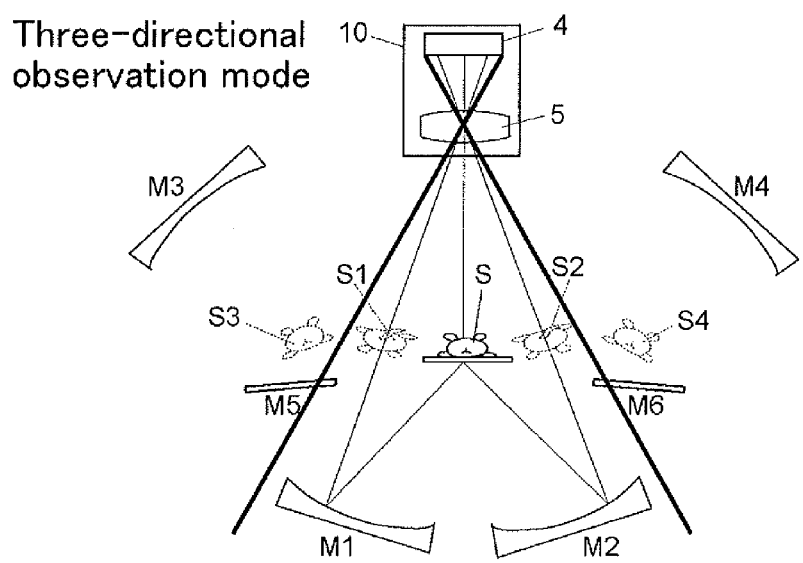
FIG. 8B is a schematic front sectional view showing the fourth embodiment in a three-directional measurement mode.
Figure 8C:
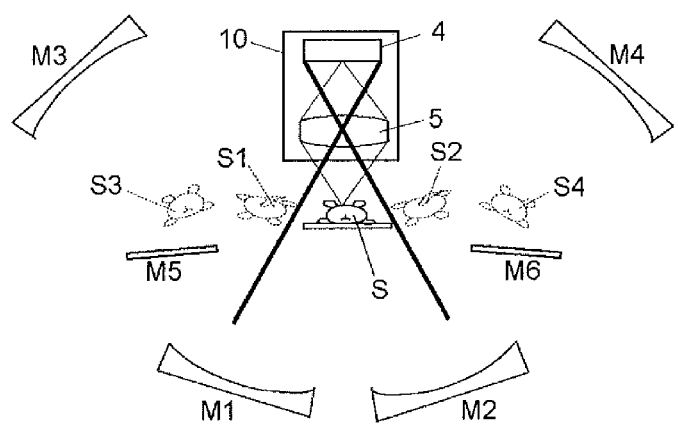
FIG. 8C is a schematic front sectional view showing the fourth embodiment in a one-directional measurement mode.

A fourth embodiment is capable of changing the number of measurement directions by changing the distance between a camera and a sample. The fourth embodiment will be described with reference to FIGS. 8A to 8D. As shown in FIGS. 8A, 8B, and 8C, selection among three cases of five-directional observation, three-directional observation, and one-directional observation can be easily performed by changing the distance between the sample S and the lens 5 by moving up and down a camera 10 including the lens 5 and the CCD 4.

Figure 8D:
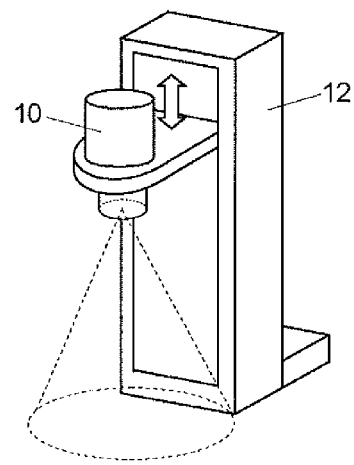
FIG. 8D is a perspective view of a camera moving system used in the fourth embodiment.

FIG. 8D shows an example of a vertical sliding system 12 for moving the camera 10, which is usually realized by a linear guide and a drive motor. When the camera 10 is moved closer to a sample, the lens 5 needs to be extended for focusing, but this is a well-known means performed manually or automatically also in commonly-used cameras.

It can be considered that it is not necessary to specifically select three-directional observation or one-directional observation as long as five-directional observation can be performed. However, it is necessary to point out that, in fact, "degree of the amount of light used" and "degree of the number of observation directions" compete against each other. More specifically, when the camera 10 is moved closer to a sample, the solid angle of the lens 5 as seen from the sample is increased, which makes it possible to guide a larger amount of light per unit area of the sample to the CCD 4 in proportion to the solid angle. Particularly, in the case of measurement of weak light emitted from a sample, the measurement time is long (e.g., 1 min or 5 min), and therefore, there is a case where the camera 10 is preferably moved closer to the sample so that the number of observation directions can be reduced and the measurement time can be shortened. On the contrary, in the case of measurement of strong light emitted from a sample, there is a case where multi-directional observation providing much information is preferably selected. Therefore, it is preferred that "degree of the amount of light used" and "degree of the number of observation directions" can be selected on a case-by-case basis in consideration of various factors such as the number of samples to be measured and allowable measurement time. This embodiment is configured to respond to such a request.

This embodiment is again summarized as follows. The optical observation system according to the fourth embodiment comprises a total of n+1 (wherein n is an integer) optical waveguide paths including: n optical waveguide paths for forming n images including at least one real image at positions having different distances from the sample S in the lateral direction of the sample S within a focal point plane of the main imaging lens 5; and an optical waveguide path receiving direct light from the sample S, wherein the main imaging lens 5 is movably supported so that the distance between the main imaging lens 5 and the sample S can be changed, and wherein the number of observation directions within the field of view of the main imaging lens 5 can also be selected from among values of (n+1) or less by changing the distance between the main imaging lens 5 and the sample S.

It can be said that this embodiment is one of the embodiments that allows a camera to sufficiently exhibit its close-up function due to the advantage of the present invention, that is, due to the advantage that it is not necessary to provide any parts such as auxiliary lenses between a sample and a camera.

Figure 9:
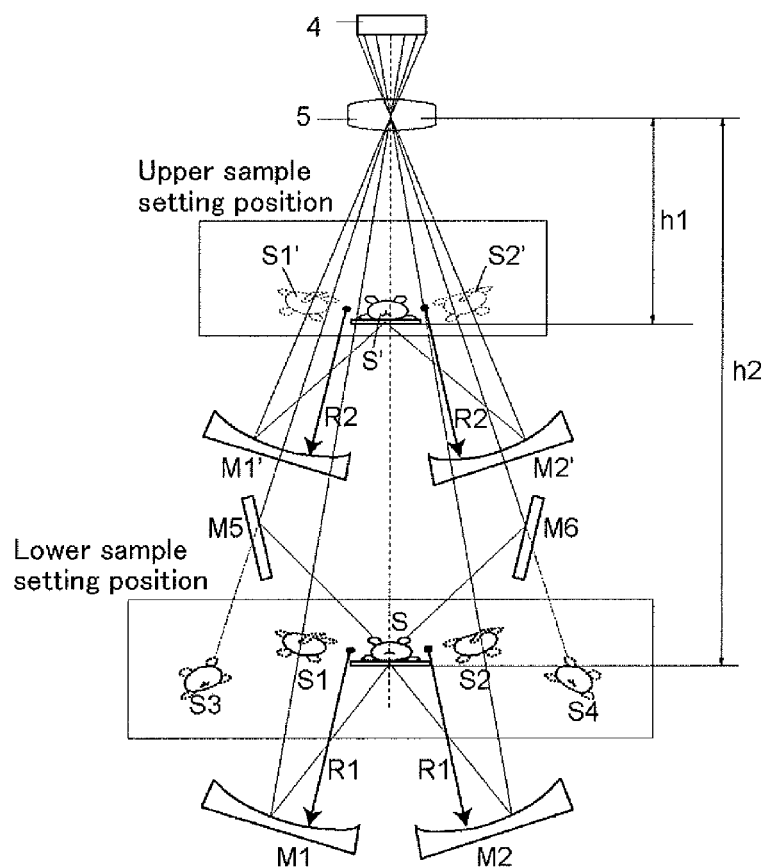
FIG. 9 is a schematic front sectional view of a variation of the fourth embodiment capable of changing the position of not a camera but a sample.

FIG. 9 is a diagram for explaining a variation of the fourth embodiment capable of changing the distance between a camera and a sample. This variation does not have a camera moving system but has an upper sample setting position (for three-directional observation) and a lower sample setting position (for five-directional observation). Therefore, the distance between a camera and a sample can be changed depending on which of the two sample setting positions is selected. When five-directional observation is selected, concave mirrors M1' and M2' used when the upper sample setting position is selected are horizontally moved automatically or manually by an escape system not to cause obstructions.

Further, as another variation, the observation range of the optical system may be changed not by changing the distance between a camera and a sample but by changing the focal length of the main imaging lens. The focal length of the main imaging lens may be changed stepwise by switching among two or more removably- or slidably-attached main imaging lens having different focal lengths. Alternatively, a variable-focal-length lens may be obviously used. Such a variable-focal-length lens may be achieved by shifting or attaching/detaching one or more of lenses constituting the main imaging lens, or may be a so-called zoom-lens capable of offering continuously variable focal lengths. Such a system for "changing the number of observation directions by changing the focal length of the main imaging lens" does not need such a camera moving system as shown in FIG. 8D used in the above-described system in which the distance between a sample and a camera can be changed, but the system of the main imaging lens becomes complicated, and therefore, production cost increases. In particular, a very bright variable-focal-length lens is generally difficult to obtain, and even if such a very bright variable-focal-length lens can be obtained, it is very expensive.

As has been described above, the sample-camera distance variable system and the variable focal length system have their respective advantages and disadvantages, but the main point of the fourth embodiment is that the number of observation directions can be changed by selecting the observation range of the optical system by using either of the two systems.

Fifth Embodiment

A fifth embodiment is capable of switching between two types of measurement modes: one for one-directional observation of two or more samples, the other for two- or more-directional observation of one sample. The fifth embodiment will be described with reference to FIGS. 10A and 10B.

Figure 10A:
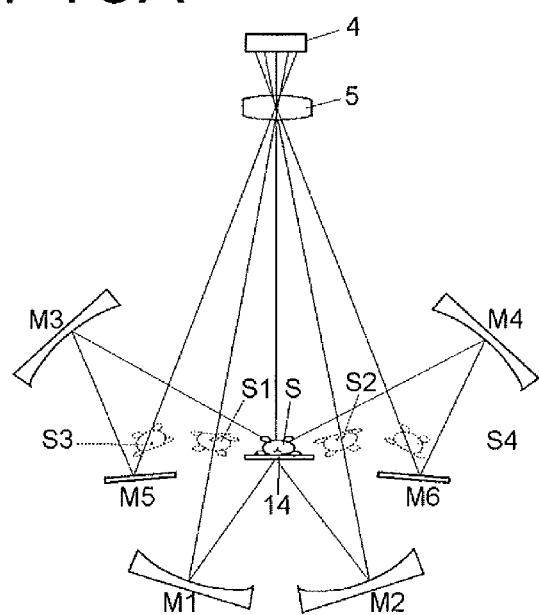
FIG. 10A is a schematic front sectional view of a fifth embodiment capable of switching between one-directional observation of two or more samples and multi-directional observation of one sample, which is in a mode where one sample is observed from five directions.
Figure 10B:
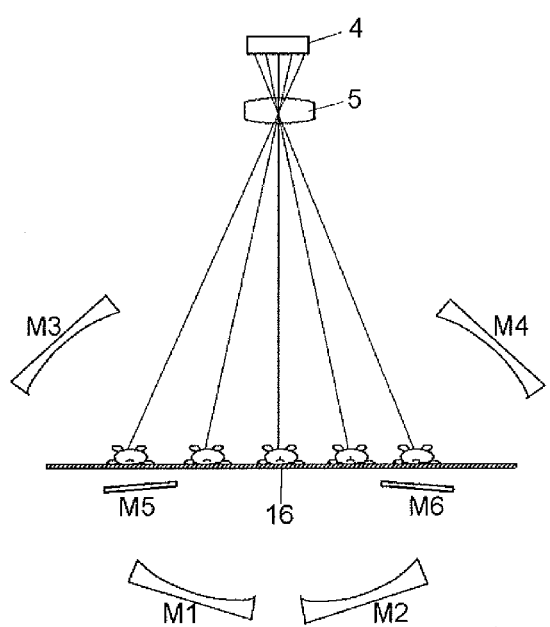
FIG. 10B is a schematic front sectional view of the fifth embodiment in a mode where two or more samples are observed from one direction.

FIG. 10A shows the optical system of the fifth embodiment when used for the above-described five-directional observation of one sample. The sample S is placed on a transparent sample stage 14. As shown in FIG. 10B, the transparent sample stage 14 can be changed to a sample stage 16 made of a light-blocking material. The sample stage 16 cuts off light beams other than light beams traveling in a direction in which the camera can directly observe the sample S, and has such a size that five mice can be placed thereon as samples. That is, one-directional simultaneous observation of 5 mice can be performed by changing the sample stage 14 to the light-blocking sample stage 16. At this time, it is not necessary to change the optical system, such as mirrors, at all. Therefore, the fifth embodiment is useful in that switching between one-directional observation of two or more samples and two- or more-directional observation of one sample can be easily performed simply by changing the sample stage of the sample holder.

Multi-directional observation is certainly effective, but when a site to be measured is already decided, there is a case where it is not necessary to specifically observe a mouse from its back side depending on the type of experiment. Therefore, according to this embodiment, a multi-directional observation mode can be switched to a one-directional observation mode when it is necessary to simultaneously measure a plurality of mice.

Also in this embodiment, the repeatedly-described advantage of the present invention, that is, the advantage that there is open-space between the sample S and the lens 5 makes it possible to perform switching between multi-directional observation and one-directional observation without any change in the optical system.

Sixth Embodiment

Figure 11A:
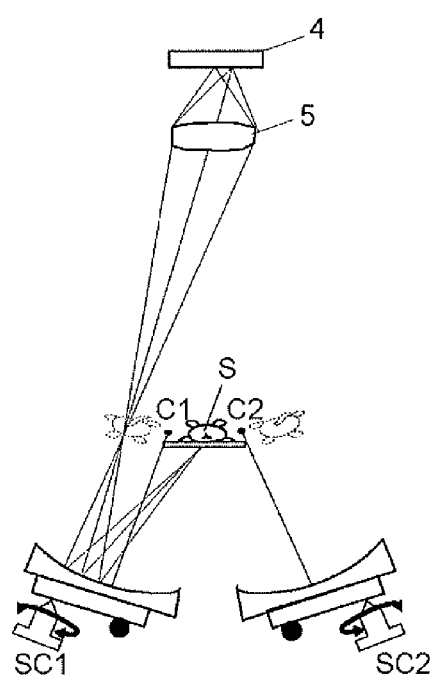
FIG. 11A is a schematic front sectional view of a sixth embodiment capable of shifting the centers of curvature of concave mirrors, wherein the centers of curvature of the concave mirrors are moved closer to a sample.
Figure 12:
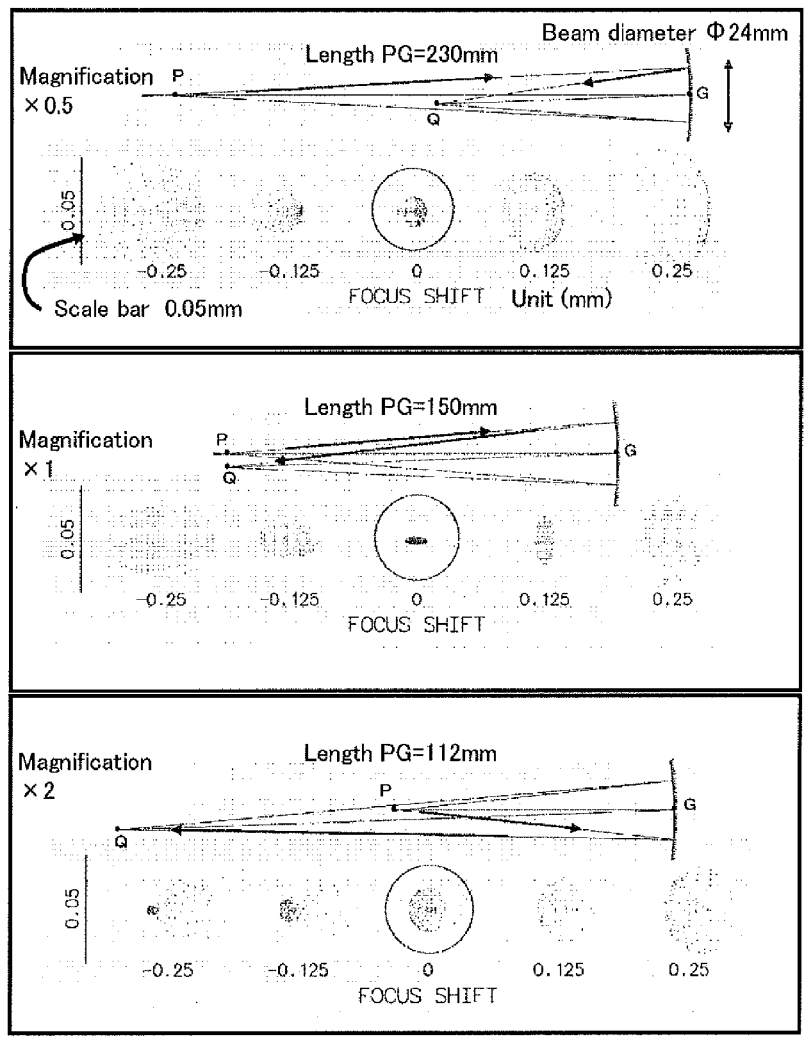
FIG. 12 is a ray trace diagram demonstrating that imaging using a spherical concave mirror at a magnification of 1:1 is particularly advantageous.
Figure 13:
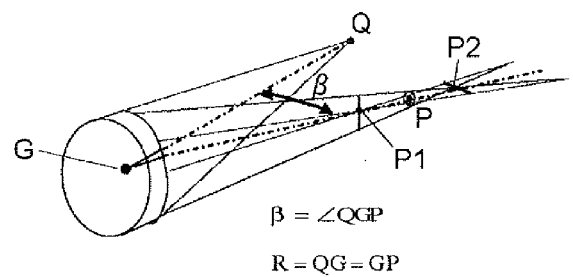
FIG. 13 is a schematic perspective view for explaining astigmatic aberration of a concave mirror.

FIG. 11A shows an embodiment capable of shifting the center of curvature C1 of a concave mirror. As has been repeatedly described above with reference to the first principle of the present invention, this embodiment utilizes the fact that a concave mirror forms a real image of a sample so that the sample and the real image are symmetrical to each other with respect to the center of curvature (e.g., C1) of the concave mirror. In this case, by shifting the center of curvature C1, it is possible to change the distance between a sample and its image formed next to the sample. As shown in FIG. 11A, the positions of centers of curvature C1 and C2 are changed by changing the angles of concave mirrors by using screws SC1 and SC2 for adjusting the position of center of curvature of the concave mirror. In the case shown in FIG. 11A, the centers of curvature C1 and C2 are close to the sample S, which is suitable for measurement of a small sample. In a case where the sample S is larger, when the sample S is measured without changing the positions of the centers of curvature C1 and C2, the sample S and its images overlap with one another. In this case, as shown in FIG. 11B, the centers of curvature C1 and C2 are moved away from the sample S to keep the images of the sample S away from the sample S. However, there is a possibility that the images are moved out of the field of view of the camera, and therefore if necessary, the camera may be elevated using a vertical camera moving system so that three images of the large sample can be displayed within the display range of the CCD 4. By combining the camera moving system for selection of the range of field of view of the camera and the system for shifting the center of curvature of a concave mirror, it is possible to most efficiently and flexibly measure a sample such as a mouse irrespective of the size of the sample.

Seventh Embodiment

Figure 14:
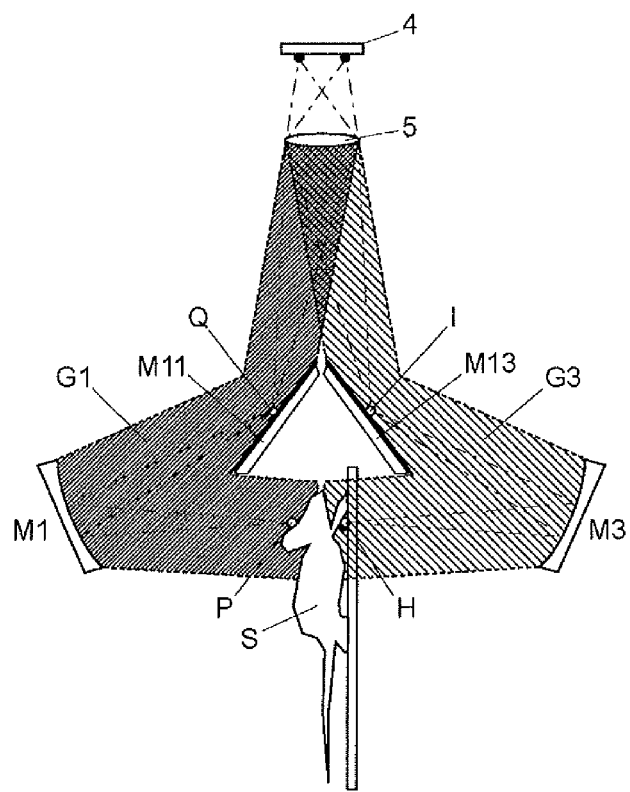
FIG. 14 is a diagram for explaining a seventh embodiment not utilizing a direct image of a sample.
Figure 15:
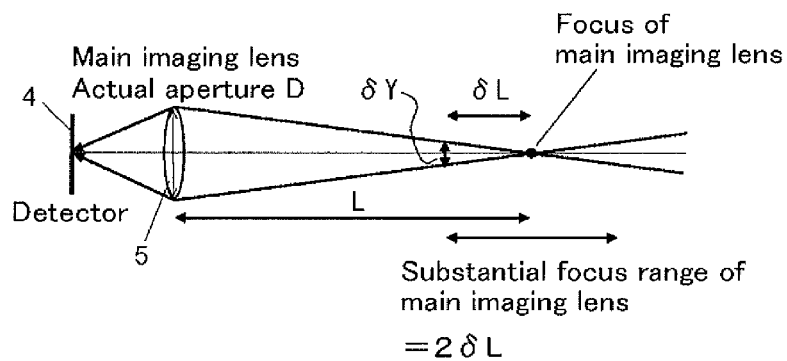
FIG. 15 is a diagram for explaining the definition of a "substantial focus range" of a main imaging lens.

As in the case of the third embodiment, a seventh embodiment is also intended to perform four-directional simultaneous observation of not the entire body of a sample but, for example, the head of a mouse. However, unlike the above-described embodiments, this embodiment does not use a directly-observed image of the sample S. The seventh embodiment will be described with reference to FIG. 14. As shown in FIG. 14, light traveling in each of four optical waveguide paths provided in four different directions is once focused midway and the resulting image is again focused by the lens 5 on the two-dimensional detector 4. Further, the difference between this embodiment and the above embodiments is that the mouse is placed not horizontally but vertically so that the body axis of the mouse is oriented toward the main imaging lens 5. The mouse may be attached to the sample holder by an appropriate tape or may be fixed to the sample holder by a fine mesh, as long as the mouse is made vertical. It is to be noted that when the drawing shown in FIG. 14 is tilted 90° to the right, the mouse can be normally, that is, horizontally placed on the sample holder.

Therefore, the point of this embodiment is that this embodiment is intended to simultaneously observe the mouse from various directions around the body axis of the mouse while the main imaging lens is arranged in the direction of the body axis of the mouse.

As shown in FIG. 14, the concave mirrors M1, M2, M3, and M4 are arranged in four different directions at 90° intervals around the body axis of the sample S. However, FIG. 14 is a sectional view taken along a direction parallel to the plane of the paper, and therefore, only the sectional views of the concave mirrors M1 and M3 are shown in FIG. 14, and the concave mirrors M2 and M4 located in a direction perpendicular to the plane of the paper are not shown in FIG. 14. More specifically, the concave mirror M2 is located in front of the plane of the paper and the concave mirror M4 is located behind the plane of the paper. Further, plane mirrors M11, M12, M13, and M14 are arranged above the sample. In FIG. 14, the sectional views of the plane mirrors M11 and M13 are shown but the plane mirrors M12 and M14 located in a direction perpendicular to the plane of the paper are not shown. More specifically, the plane mirror M12 is located in front of the plane of the paper and the plane mirror M14 is located behind the plane of the paper. The four plane mirrors M11, M12, M13, and M14 each have a triangular shape, and are arranged so that the four triangles form a quadrangular pyramid. The sectional view of the quadrangular pyramid is given by the plane mirrors M11 and M13 in FIG. 14. Further, in FIG. 14, the sections of two optical waveguide paths G1 and G3 on the plane of the paper are marked with diagonal lines.

Light emitted from a point P on the sample S is reflected by the concave mirror M1, is once focused on a point Q, is further reflected by the plane mirror M11 toward the lens 5, and is finally focused by the lens 5 on the CCD 4. More specifically, a plurality of light beams traveling from the sample S toward the concave mirror M1 are once focused on some point near the plane mirror M11 in the optical waveguide path G1 (marked with diagonal lines), and are then finally focused on part of the CCD 4 so that an image of the head of the mouse as the sample S is formed. Likewise, light emitted from a point H located on the back side (right side) of the head of the mouse is reflected by the concave mirror M3, is focused on a point I near the plane mirror M13, and travels toward the lens 5 while again diffusing, and is finally focused by the lens 5 on one point on the CCD 4. Therefore, a plurality of light beams traveling from the sample S toward the concave mirror M3 are once focused on some point near the plane mirror M13 in the optical waveguide path G3, and are then finally focused on part of the CCD 4 so that an image of the head of the mouse is formed. Optical waveguide paths G2 and G4 (not shown) extend from the sample S toward the front side of the plane of the paper and toward the back side of the plane of the paper, respectively. Light beams traveling in the optical waveguide path G2 are reflected by the concave mirror M2 located in front of the plane of the paper, and are then again reflected by the plane mirror M12 constituting the quadrangular pyramid, and are then finally focused by the lens 5 on the CCD 4. Light beams traveling in the optical waveguide path G4 are reflected by the concave mirror M4 located behind the plane of the paper, and are then again reflected by the plane mirror M14 constituting the quadrangular mirror M14, and are then finally focused by the lens 5 on the CCD 4.

As described above, four images of the head of the mouse observed from four directions are once formed in the four optical waveguide paths provided at 90° intervals around the body axis of the sample S (mouse), and are then again formed by the lens 5 on the CCD 4.

As has been described above, light traveling directly from the sample S toward the lens 5 is blocked by the plane mirrors M11, M12, M13, and M14 constituting a quadrangular pyramid and is therefore not used for imaging.

The feature of the seventh embodiment is that four images of a sample (mouse) observed from four directions perpendicular to the body axis of the mouse are formed by the optical system symmetrical with respect to the body axis of the mouse and a direct image of the sample in the direction of the body axis is not measured.

It is to be noted that the seventh embodiment has been described with reference to a case where concave mirrors are arranged at 90° intervals around the body axis of the sample, but the number of divisions may be increased or decreased. For example, concave mirrors may be arranged at 60° intervals. In this case, the sample S (mouse) is observed from six directions, and therefore, six concave mirrors are arranged around the body axis of the mouse, and six plane mirrors are arranged above the head of the mouse so that a six-sided pyramid is formed.

Figure 17:
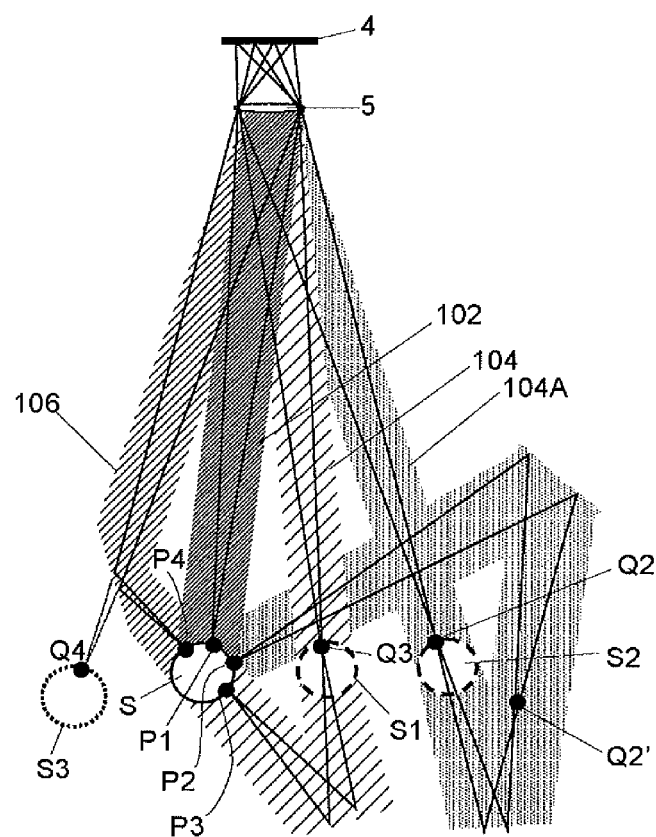
FIG. 17 is a conceptual diagram for explaining the difference among three types of optical waveguide paths.

Finally, the types of optical waveguide paths described above with reference to FIG. 17 and the number of optical waveguide paths of each of the above embodiments are summarized as follows.

The first embodiment (FIG. 4A) has a total of five optical waveguide paths including one Type 1 optical waveguide path and four Type 2 optical waveguide paths.

The second embodiment (FIG. 6A) has a total of five optical waveguide paths including one Type 1 optical waveguide path, two Type 2 optical waveguide paths, and two Type 3 optical waveguide paths.

The third embodiment (FIG. 7A) has a total of four optical waveguide paths including one Type 1 optical waveguide path and three Type 2 optical waveguide paths.

The fourth embodiment (FIGS. 8A, 8B, and 8C) has a total of five optical waveguide paths including one Type 1 optical waveguide path and four Type 2 optical waveguide paths, one or more of which are appropriately selected by selecting the field of view of the main imaging lens.

The variation of the fourth embodiment (FIG. 9) has a total of five optical waveguide paths including one Type 1 optical waveguide path, two Type 2 optical waveguide paths, and two Type 3 optical waveguide paths, three or five of which are selected according to the position of a sample.

The fifth embodiment uses a total of five optical waveguide paths including one Type 1 optical waveguide path and four Type 2 optical waveguide paths only when a multi-directional observation mode is selected.

The sixth embodiment has a total of three optical waveguide paths including one Type 1 optical waveguide path and two Type 2 optical waveguide paths.

The seventh embodiment does not have a Type 1 optical waveguide path but has only four Type 2 optical waveguide paths.

As described above, all the embodiments absolutely have the Type 2 optical waveguide path, but not all the embodiments have the Type 1 optical waveguide path and/or the Type 3 optical waveguide path.

Further, all first to seventh embodiments have been described with reference to a typical case of using one camera (which refers to a combination of the main imaging lens and the two-dimensional detector), but it goes without saying that the present invention applies also to a case where two or more cameras are used. For example, the load of receiving images guided by six optical waveguide paths provided in different directions may be shared between two cameras. In this case, for example, a first camera may receive images guided by three optical waveguide paths and a second camera may receive images guided by the remaining three optical waveguide paths. Each of the cameras is configured to simultaneously receive light from specified two or more directions and to form images at different positions on the two-dimensional detector.

Figure 1A:
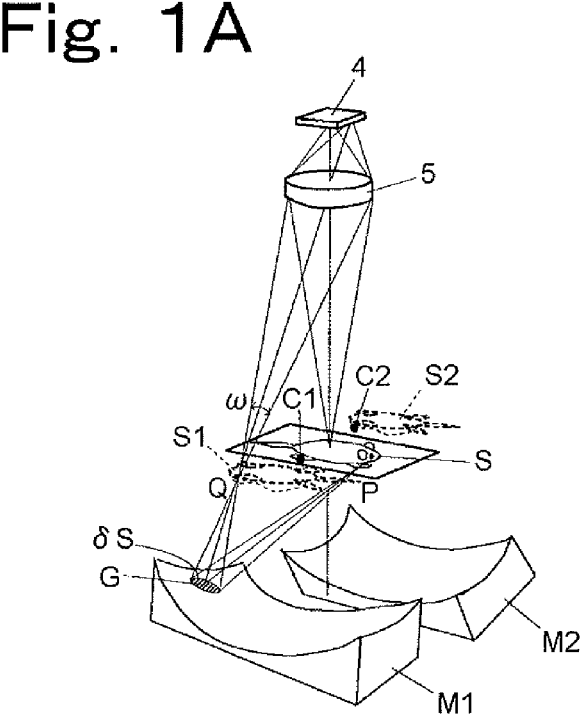
FIG. 1A is a schematic perspective view for explaining a first principle of the present invention.
Figure 1B:
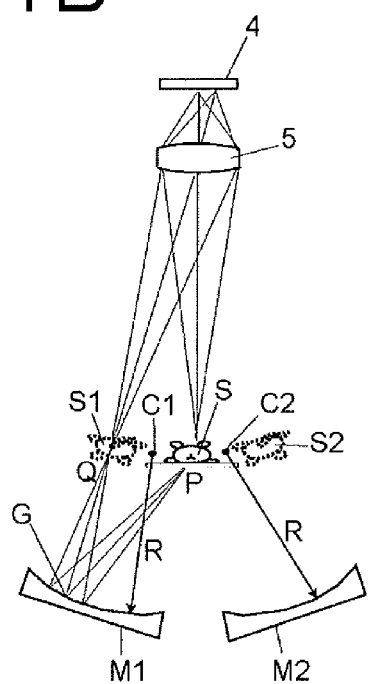
FIG. 1B is a schematic front sectional view for explaining the first principle of the present invention.
Figure 1D:
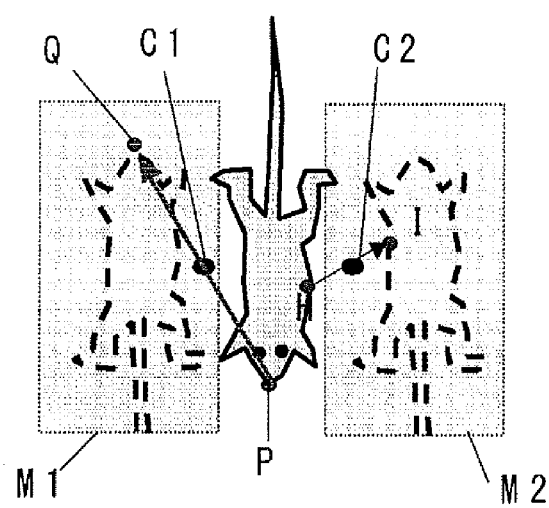
FIG. 1D is a plan view showing a sample and its images viewed through a lens arranged above the sample in the theoretical diagram.

Further, as a variation, the optical system shown in FIG. 1B may be modified by additionally providing a second camera between the concave mirror M1 and the concave mirror M2 to pick up the image of the sample S observed from directly below. When the camera (i.e., a combination of the main imaging lens 5 and the CCD 4) shown in FIG. 1B is defined as a first camera, the first camera is responsible for measurement from three directions (from above, obliquely lower right, and obliquely lower left) and the second camera is responsible for measurement from directly below, and therefore, the sample S can be observed from four directions in total. In this case, the second camera is responsible for measurement from only one direction, and therefore, the present invention does not apply to the second camera. However, the present invention applies to the first camera, and therefore, the system as a whole is configured to simultaneously receive images of light guided by optical waveguide paths provided in specified two or more directions and to form images at different positions on the two-dimensional detector.

For that matter, even in a case where only one camera is used, there is a case where two or more optical waveguide paths provided in two or more specified directions are selected from all the optical waveguide paths provided and light from the two or more specified directions is simultaneously received. For example, the embodiment shown in FIGS. 8A and 8B has five optical waveguide paths in total, but in addition to a case where, as shown in FIG. 8A, all five optical waveguide paths are used. There is also a case where, as shown in FIG. 8B, the rightmost and leftmost two optical waveguide paths are not used and light from only three of the five optical waveguide paths is received. Based on the above description, the point of the present invention is again summarized as follows. A plurality of optical waveguide paths are prepared in different directions, and images observed from two or more directions guided by all or, in some cases, some (i.e., two or more) of the optical waveguide paths are formed at different positions on a two-dimensional detector, and one or more of all the optical waveguide paths are of Type 2 shown in FIG. 17. That is, in at least one optical waveguide path, light is at least focused once and is then finally focused on the two-dimensional detector.

The invention claimed is:

1. A biological imaging device comprising:
    a sample holder for holding a biological sample placed thereon;
    a two-dimensional detector for detecting an image of light emitted from the sample placed on the sample holder;
    optical waveguide paths for observing the sample placed on the sample holder from two or more directions and for guiding images of light emitted from the sample in different directions to the two-dimensional detector, the optical waveguide paths being provided in different directions; and
    a main imaging lens arranged between the two-dimensional detector and the optical waveguide paths for forming images guided by the optical waveguide paths at different positions on the two-dimensional detector according to an observation direction,
    wherein at least one of the optical waveguide paths is an optical waveguide path not receiving direct light from the sample, and the optical waveguide path(s) not receiving direct light from the sample includes an optical element arranged to form an image of the sample within a substantial focus range of the main imaging lens and to allow light beams from the image to travel toward the main imaging lens, and the optical element is an optical element that forms a real image as the image, so that the main imaging lens simultaneously forms images observed from two or more directions and guided by the optical waveguide paths on the two-dimensional detector.

2. The biological imaging device according to claim 1, wherein the optical waveguide paths include an optical waveguide path receiving direct light from the sample other than the optical waveguide path(s) not receiving direct light from the sample.

3. The biological imaging device according to claim 1, wherein each of the optical waveguide path(s) not receiving direct light from the sample includes an optical element that forms a real image as the image.

4. The biological imaging device according to claim 1, wherein the optical element for forming the real image of the sample within a substantial focus range of the main imaging lens is a concave mirror.

5. The biological imaging device according to claim 4,
    wherein at least one of the optical waveguide paths including the concave mirror further includes a plane mirror, and
    wherein the real image of the sample is formed by the concave mirror and the plane mirror within a substantial focus range of the main imaging lens.

6. The biological imaging device according to claim 4,
    wherein the optical waveguide paths include an optical waveguide path receiving direct light from the sample and one or two optical waveguide paths in which the concave mirror is provided to form a real image of the sample next to the sample, and
    wherein a directly-observed image of the sample and a real image(s) of the sample formed next to the sample are focused by the main imaging lens on the two-dimensional detector to simultaneously observe the sample from two or three directions.

7. The biological imaging device according to claim 4, wherein the at least one optical waveguide path containing the concave mirror includes an adjustment system capable of mechanically moving a position of the center of curvature of the concave mirror to move a position of a real image formed by the concave mirror.

8. The biological imaging device according to claim 1,
    wherein, when a direction in which the main imaging lens and the two-dimensional detector are provided is defined as a direction directly above the sample, as the optical waveguide paths, five optical waveguide paths are provided to acquire a total of five images observed from five directions formed on the two-dimensional detector, which include a directly-observed image of the sample formed at the center of the two-dimensional detector, two images observed from two obliquely downward directions of the sample formed on opposite sides of the directly-observed image, and two images observed from obliquely upward directions of the sample formed on opposite sides of the two images.

9. The biological imaging device according to claim 1,
    wherein, when a direction in which the main imaging lens and the two-dimensional detector are provided is defined as a direction directly above the sample, as the optical waveguide paths, four optical waveguide paths are provided to acquire a total of four images observed from four directions (i.e., from above, below, right, and left) formed on the two-dimensional detector, which include a directly-observed image of the sample formed at the center of the two-dimensional detector, two images of the sample observed from two lateral directions formed on opposite sides of the directly-observed image, and an image observed from below the sample formed next to the directly-observed image in a direction perpendicular to a direction in which the two images observed from two lateral directions are formed.

10. The biological imaging device according to claim 1, wherein, when n is an integer, as the optical waveguide paths, a total of (n+1) optical waveguide paths including: n optical waveguide paths not receiving direct light from the sample, which are provided to form images of the sample at positions having different distances from the sample in a lateral direction of the sample within a focal point plane of the main imaging lens; and an optical waveguide path receiving direct light from the sample are provided, wherein the main imaging lens or the sample is movably supported so that a distance between the main imaging lens and the sample is variable, and wherein the number of observation directions within a field of view of the main imaging lens is selected from among values of (n+1) or less by changing or selecting a distance between the main imaging lens and the sample.

11. The biological imaging device according to claim 10, wherein as the optical waveguide paths, four optical waveguide paths are provided so that a total of four images of the sample, including two images formed on opposite sides of the sample and two images formed on opposite sides of the two images, are formed in line within a plane including a plane on which the sample is placed, and wherein two or more observation modes are selected from among five-directional simultaneous observation, three-directional simultaneous observation, and one-directional observation by changing a distance between the main imaging lens and the sample.

12. The biological imaging device according to claim 1, wherein as the optical waveguide paths, two or more optical waveguide paths are provided so as to form two or more real images of the sample in a lateral direction of the sample, wherein the sample holder has, as removable sample stages, a light-blocking sample stage, which avoids formation of all the real images and has such a size that two or more samples are placed thereon, and a light-permeable sample state, and wherein an observation mode is switchable between one-directional observation of two or more samples using the light-blocking sample stage and multi-directional observation of one sample using the light-permeable sample stage.

13. The biological imaging device according to claim 1, wherein at least one of the optical waveguide path(s) not receiving direct light from the sample includes only a plane mirror to form a virtual image as the image.

14. The biological imaging device according to claim 13, wherein the remaining optical waveguide path(s) not receiving direct light from the sample includes/include a concave mirror as the optical element for forming a real image of the sample within a substantial focus range of the main imaging lens.

15. The biological imaging device according to claim 14, wherein at least one of the optical waveguide path(s) containing the concave mirror further includes a plane mirror, so that a real image of the sample is formed by the concave mirror and the plane mirror within a substantial focus range of the main imaging lens.

16. The biological imaging device according to claim 14, wherein at least one optical waveguide path containing the concave mirror includes an adjustment system capable of mechanically moving a position of the center of curvature of the concave mirror to move a position of a real image formed by the concave mirror.

17. The biological imaging device according to claim 13, wherein, when a direction in which the main imaging lens and the two-dimensional detector are provided is defined as a direction directly above a sample, as the optical waveguide paths, five optical waveguide paths are provided to acquire a total of five images observed from five directions formed on the two-dimensional detector, which include a directly-observed image of the sample formed at the center of the two-dimensional detector, two images observed from two obliquely downward directions of the sample formed on opposite sides of the directly-observed image, and two images observed from two obliquely upward directions of the sample formed on opposite sides of the two images.

18. The biological imaging device according to claim 13, wherein, when a direction in which the main imaging lens and the two-dimensional detector are provided is defined as a direction directly above the sample, as the optical waveguide paths, four optical waveguide paths are provided to acquire a total of four images observed from four directions (i.e., from above, below, right, and left) formed on the two-dimensional detector, which include a directly-observed image of the sample formed at the center of the two-dimensional detector, two images observed from two lateral directions of the sample formed on opposite sides of the directly-observed image, and an image observed from below the sample formed next to the directly-observed image in a direction perpendicular to a direction in which the two images observed from two lateral directions are formed.

19. The biological imaging device according to claim 1, wherein, when n is an integer, as the optical waveguide paths, a total of (n+1) optical waveguide paths including: n optical waveguide paths not receiving direct light from the sample, which are provided to form images of the sample at positions having different distances from the sample in a lateral direction of the sample within a focal point plane of the main imaging lens; and an optical waveguide path receiving direct light from the sample are provided, and wherein the number of observation directions within a field of view of the main imaging lens is selected from among values of (n+1) or less by changing a focal length of the main imaging lens.

20. The biological imaging device according to claim 19, wherein, as the optical waveguide paths, four optical waveguide paths are provided so that a total of four images of the sample, including two images formed on opposite sides of the sample and two images formed on opposite sides of the two images, are formed in line within a plane including a plane on which the sample is placed, and wherein two or more observation modes are selected from among five-directional simultaneous observation, three-directional simultaneous observation, and one-directional observation by changing a focal length of the main imaging lens.

21. The biological imaging device according to claim 1, wherein, as the optical waveguide path, only the optical waveguide path(s) including a concave mirror and a plane mirror and not receiving direct light from the sample is included.

22. The biological imaging device according to claim 1, further comprising an excitation light source which emits fluorescence excitation light to irradiate the sample with the fluorescence excitation light and a filter provided between the sample and the main imaging lens to remove a wavelength component of the excitation light source.

23. The biological imaging device according to claim 1, further comprising a display unit for displaying acquired multi-directional images and image converting means which performs any one or more of changes in display order and image orientation, inversion, rotation, size adjustment, and distortion correction on the images to be displayed on the display.

* * * * *